US007923564B2

(12) United States Patent
Thygesen et al.

(10) Patent No.: US 7,923,564 B2
(45) Date of Patent: *Apr. 12, 2011

(54) SYNTHESIS OF N-(4-FLUOROBENZYL)-N-(1-METHYLPIPERIDIN-4-YL)-N'-(4-(2-METHYLPROPYLOXY)PHENYLMETHYL)CARBAMIDE AND ITS TARTRATE SALT AND CRYSTALLINE FORMS

(75) Inventors: Mikkel Boas Thygesen, Copenhagen East (DK); Nathalie Schlienger, Frederiksberg (DK); Bo-Ragnar Tolf, Malmö (SE); Carl-Magnus A. Andersson, Hjärup (SE); Fritz Blatter, Reinach (CH); Jörg Berghausen, Lörrach (DE)

(73) Assignee: ACADIA Pharmaceuticals, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/795,547

(22) Filed: Jun. 7, 2010

(65) Prior Publication Data

US 2010/0305329 A1 Dec. 2, 2010

Related U.S. Application Data

(63) Continuation of application No. 11/235,558, filed on Sep. 26, 2005, now Pat. No. 7,732,615.

(60) Provisional application No. 60/614,014, filed on Sep. 27, 2004.

(51) Int. Cl.
*C07D 211/56* (2006.01)
(52) U.S. Cl. ...................................................... 546/223
(58) Field of Classification Search .................... 546/223
See application file for complete search history.

(56) References Cited

U.S. PATENT DOCUMENTS

| | | | |
|---|---|---|---|
| 3,983,234 A | 9/1976 | Sayers |
| 4,138,492 A | 2/1979 | Noverola et al. |
| 4,255,432 A | 3/1981 | Kluge et al. |
| 4,332,804 A | 6/1982 | Clark |
| 4,353,900 A | 10/1982 | Clark |
| 4,353,901 A | 10/1982 | Clark |
| 4,367,232 A | 1/1983 | Boix-Igleasias et al. |
| 4,853,394 A | 8/1989 | King et al. |
| 5,025,013 A | 6/1991 | Barreau et al. |
| 5,214,055 A | 5/1993 | Peglion et al. |
| 5,216,165 A | 6/1993 | Mobilio et al. |
| 5,461,066 A | 10/1995 | Gericke et al. |
| 5,595,872 A | 1/1997 | Wetterau, II et al. |
| 5,621,010 A | 4/1997 | Sueda et al. |
| 5,707,798 A | 1/1998 | Brann |
| 5,795,894 A | 8/1998 | Shue et al. |
| 5,869,488 A | 2/1999 | Shue et al. |
| 5,877,173 A | 3/1999 | Olney et al. |
| 5,912,132 A | 6/1999 | Brann |
| 5,955,281 A | 9/1999 | Brann |
| 6,107,324 A | 8/2000 | Behan et al. |
| 6,140,509 A | 10/2000 | Behan et al. |
| 6,150,393 A | 11/2000 | Behan et al. |
| 6,214,846 B1 | 4/2001 | Elliott |
| 6,358,698 B1 | 3/2002 | Weiner et al. |
| 6,756,393 B2 | 6/2004 | Andersson et al. |
| 6,815,458 B2 | 11/2004 | Andersson et al. |
| 6,911,452 B2 | 6/2005 | Schlienger |
| 7,022,698 B2 | 4/2006 | Hamied et al. |
| 7,041,667 B1 | 5/2006 | Armour et al. |
| 7,115,634 B2 | 10/2006 | Thurieau et al. |
| 7,253,186 B2 | 8/2007 | Andersson et al. |
| 7,601,740 B2 | 10/2009 | Weiner et al. |
| 7,732,615 B2 | 6/2010 | Thygesen et al. |
| 2004/0006081 A1 | 1/2004 | Burrows et al. |
| 2004/0106600 A1 | 6/2004 | Andersson et al. |
| 2004/0213816 A1 | 10/2004 | Weiner et al. |
| 2005/0014757 A1 | 1/2005 | Andersson et al. |
| 2005/0148018 A1 | 7/2005 | Weiner et al. |
| 2005/0244862 A1 | 11/2005 | Brann |
| 2005/0256108 A1 | 11/2005 | Schlienger |
| 2005/0261340 A1 | 11/2005 | Weiner et al. |
| 2005/0288328 A1 | 12/2005 | Weiner et al. |
| 2006/0094758 A1 | 5/2006 | Andersson et al. |
| 2006/0106063 A1 | 5/2006 | Thygesen et al. |
| 2006/0111399 A1 | 5/2006 | Thygesen et al. |
| 2006/0194778 A1 | 8/2006 | Andersson et al. |
| 2006/0194834 A1 | 8/2006 | Andersson et al. |
| 2006/0199794 A1 | 9/2006 | Schlienger |
| 2006/0199818 A1 | 9/2006 | Andersson et al. |
| 2006/0199842 A1 | 9/2006 | Weiner et al. |

(Continued)

FOREIGN PATENT DOCUMENTS

CA 984843 3/1976

(Continued)

OTHER PUBLICATIONS

Adam, et al. 1989. Effects of repeated ritanserin on middle-aged poor sleepers. *Psychopharmacology*, 99:219-221. Adell, et al. 2005. Strategies for producing faster acting antidepressants. *Drug Discovery Today*, 10(8):578-585.
Akin, et al. 2004. Decreased serotonin $5-HT_{2A}$ receptor-stimulated phosphoinositide signaling in fibroblasts from melancholic depressed patients. *Neuropsychopharmacology*, 29:2081-2087.
Alvisi, N. 1892. Sulla formazione di derivati pirazolici dalle dicloridrine e dalla tribromidrina della glicerina ordinaria, *Gazz. Chem. Ital.* 22:158-168.

(Continued)

*Primary Examiner* — Rita J Desai
*Assistant Examiner* — John Mabry
(74) *Attorney, Agent, or Firm* — Jones Day

(57) ABSTRACT

Disclosed herein are methods for synthesizing N-(4-fluorobenzyl)-N-(1-methylpiperidin-4-yl)-N'-(4-(2-methylpropyloxy)-phenylmethyl)carbamide. Also disclosed herein is the hemi-tartrate salt of N-(4-fluorobenzyl)-N-(1-methylpiperidin-4-yl)-N'-(4-(2-methylpropyloxy)-phenylmethyl)carbamide and methods for obtaining the salt. Further disclosed are various crystalline forms of N-(4-fluorobenzyl)-N-(1-methylpiperidin-4-yl)-N'-(4-(2-methylpropyloxy)-phenylmethyl)carbamide and its hemi-tartrate salt including various polymorphs and solvates.

6 Claims, 4 Drawing Sheets

U.S. PATENT DOCUMENTS

| | | | |
|---|---|---|---|
| 2006/0205710 | A1 | 9/2006 | Schlienger et al. |
| 2006/0205722 | A1 | 9/2006 | Andersson et al. |
| 2006/0205780 | A1 | 9/2006 | Thygesen et al. |
| 2006/0205781 | A1 | 9/2006 | Thygesen et al. |
| 2006/0264465 | A1 | 11/2006 | Weiner et al. |
| 2006/0264466 | A1 | 11/2006 | Weiner et al. |
| 2006/0286610 | A1 | 12/2006 | Brann |
| 2006/0292606 | A1 | 12/2006 | Brann |

FOREIGN PATENT DOCUMENTS

| | | |
|---|---|---|
| EP | 0 005 318 A1 | 11/1979 |
| EP | 0 061 333 A1 | 9/1982 |
| EP | 0 379 441 A1 | 7/1990 |
| EP | 0 548 015 A1 | 6/1993 |
| EP | 0 260 070 B1 | 8/1993 |
| EP | 0 625 507 A2 | 11/1994 |
| FR | 2802206 A1 | 6/2001 |
| HU | 157325 | 3/1998 |
| WO | WO 94/27967 A1 | 12/1994 |
| WO | WO 97/08166 A1 | 3/1997 |
| WO | WO 97/11940 A1 | 4/1997 |
| WO | WO 97/38665 A2 | 10/1997 |
| WO | WO 97/38984 A1 | 10/1997 |
| WO | WO 98/11128 A1 | 3/1998 |
| WO | WO 98/17646 A1 | 4/1998 |
| WO | WO 98/44921 A1 | 10/1998 |
| WO | WO 98/50534 A1 | 11/1998 |
| WO | WO 99/52927 A1 | 10/1999 |
| WO | WO 00/23076 A1 | 4/2000 |
| WO | WO 00/56335 A1 | 9/2000 |
| WO | WO 00/59497 A1 | 10/2000 |
| WO | WO 00/69810 A1 | 11/2000 |
| WO | WO 01/44191 A1 | 6/2001 |
| WO | WO 01/66521 A1 | 9/2001 |
| WO | WO 01/87839 A1 | 11/2001 |
| WO | WO 02/079186 A2 | 10/2002 |
| WO | WO 03/057698 A2 | 7/2003 |
| WO | WO 03/057698 A3 | 7/2003 |
| WO | WO 03/062206 A2 | 7/2003 |
| WO | WO 03/062206 A3 | 7/2003 |
| WO | WO 03/070246 A1 | 8/2003 |
| WO | WO 03/086400 A1 | 10/2003 |
| WO | WO 2004/000808 A2 | 12/2003 |
| WO | WO 2004/000808 A3 | 12/2003 |
| WO | WO 2004/009549 A2 | 1/2004 |
| WO | WO 2004/064738 A2 | 8/2004 |
| WO | WO 2004/064738 A3 | 8/2004 |
| WO | WO 2004/064753 A2 | 8/2004 |
| WO | WO 2004/072034 A1 | 8/2004 |
| WO | WO 2005/063254 A2 | 7/2005 |
| WO | WO 2005/112927 A | 12/2005 |
| WO | WO 2006/036874 A1 | 4/2006 |
| WO | WO 2006/037043 A1 | 4/2006 |
| WO | WO 2004/039322 A2 | 5/2007 |

OTHER PUBLICATIONS

Antilla, et al. 2001. Copper-catalyzed coupling of arylboronic acids and amines. *Organic Letters*, 3(13):2077-2079.

Antilla, et al. 2002. The copper-catalyzed N-arylation of indoles. *J. Am. Chem. Soc.*, 124:11684-11688.

Archibald, et al., 1974 "Benzamidopiperdines. 2. Heterocyclic Compounds Related to Indoramin" *J. Medicinal Chemistry*, 17(7):736-739.

Archibald, et al., 1974 "Benzamidopiperdines. 3. Heterocyclic Compounds Related to Indoramin" J. Medicinal Chemistry, 17(7):-739-744.

Archibald, et al., 1974 "1.4-Bis-(2-indol-3-ylethyl)piperdines" J. Medicinal Chemistry, 17(7):-745-747.

Artico, et al. 1992. Aromatic hydrazides as specific inhibitors of bovine serum amine oxidase. *Eur. J. Med. Chem.*, 27;219-228.

Bakshi, et al. 1994. Clozapine antagonizes phencyclidine-induced deficits in sensorimotor gating of the startle response. *The Journal of Pharmacology and Experimental Therapeutics*, 271(2):787-794.

Barchas, J. 1973. *Serotonin and Behavior*. New York: Academic Press.

Barnes, et al. 1999. A review of central 5-HT receptors and their function. *Neuropharmacology*, 38:1083-1152.

Barr, et al. 1997. Agonist-independent activation of $G_z$ by the 5-hydroxytryptamine$_{1A}$ receptor co-expressed in *Spodoptero frugiperda* cells. *The Journal of Biological Chemistry*, 272(52):32979-32987.

Bassus, et al. 1974. Psychotropes potentiels. X. Synthèse de butyrophénones à cycle pipéridine-spiro-tétrahydrooxazinone douées d'activité neuroleptique. *Eur. J. Med. Chem.—Chimica Therapeutica*, 9(4):416-423.

Bennett, et al. 1993. Suppression of dyskinesias in advanced Parkinson's disease. II. Increasing daily clozapine doses suppress dyskinesias and improve parkinsonism symptoms. *Neurology*, 43:1551-1555.

Berge etal J. Pharm Sci. 1977, 66,1 -19.

Bhatia, et al. 1996. 5-Lipoxygenase inhibitors: Synthesis and structure-activity relationships of a series of 1-Aryl-2H,4H-tetrahydro-1,2,4-triazin-3-ones. *J. Med. Chem.*, 39:3938-3950.

Biagi, et al. 1988. 1,2,3-Triazoles: Structural changes on two effective inhibitors of the prostaglandin synthesis in vitro. *Farmaco Ed. Sci.*, 43:597-612.

Bibbiani, et al. 2001. Serotonin 5-HT1 A agonist improves motor complications in rodent and primate parkinsonian models. *Neurology*, 57:1829-1834.

Birkmayer, et al. 1974. Nucleus ruber and L-Dopa psychosis: Biochemical post-mortem findings. *Journal of Neural Transmission*, 35:93-116.

Blakley, et al. 2001. Bidirectional changes in ethanol consumption in rats with site-specific antisense down-regulation of 5-hydroxytryptamine$_{2A}$ receptors in brain. *The Journal of Pharmacology and Experimental Therapeutics*, 299(1):277-289.

Blier, et al. 2001. Putative mechanisms of action of antidepressant drugs in affective and anxiety disorders and pain. *Journal of Psychiatry & Neuroscience*, 26(1):37-43.

Blier, et al. 2005. Potential mechanisms of action of atypical antipsychotic medications in treatment-resistant depression and anxiety. *J. Clin. Psychiatry*, 66(suppl 8):30-40.

Bond et al. 1995. Physiological effects of inverse agonists in transgenic mice with myocardial overexpression of the $β_2$-adrenoceptor. *Nature*, 374:272-276.

Boullin D. J. 1978. *Serotonin in Mental Abnormalities* (p. 316). New York: Wiley.

Brown, et al. 1924. Catalytic alkylation of aniline, *J. Am. Chem. Soc.*, 46(8):1836-1839.

Buchi et al. 1969. Synthesis of (±)-nuciferal. *J. Org. Chem.*, 34(4):1122-1123.

Butcher, et al. 1970. L-Dopa induced changes in central monoamine neurons after peripheral decarboxylase inhibition. *Letters to the Editor, J. Pharm. Pharmac.*, 22:313-316.

Buu-Hoi, et al. 1951. Further studies in the alkylation of phenols and thiophenols, *J. Org. Chem.*, 16:988-994.

Cacchi, et al. 2003. Palladium-catalyzed reaction of aryl iodides with acetic anhydride. A carbon monoxide-free synthesis of acetophenones. *Organic Letters*, 5(3):289-291.

Carman, et al. 1998. A further synthesis of an analogue of the antifungal/antiherbivore lipid from avocado. *Aust. J. Chem.*, 51:955-959.

Caroon, et al. 1981, Synthesis and antihypertensive activity of a series of 8-substituted 1-Oxa-3,8-diazaspiro[4.5]decan-2-ones. *J. Med. Chem.*, 24:1320-1328.

Carroll, et al. 1992. Synthesis and muscarinic receptor activity of ester derivatives of 2-substituted 2-azabicyclo[2.2.1]heptan-5-ol and -6-ol. *J. Med. Chem.*, 35:2184-2191.

Catarzi, et al. 2001. Synthesis, ionotropic glutamate receptor binding affinity, and structure-activity relationships of a new set of 4,5-dihydro-8-heteroaryl-4-oxo-1,2,4-triazolo[1,5-α]quinoxaline-2-carboxylates analogues of TQX-173. *J. Med Chem.*, 44:3157-3165.

Cerione, et al. 1984. The mammalian $β_2$-adrenergic receptor: Reconsitution of functional interactions between pure receptor and pure stimlatory nucelotide binding protein of the adenylate cyclase system. *Biochemistry*, 23:4519-4525.

Chemical Abstracts, 73:25305. Benke, et al. 1970.

Chemical Abstracts, 128:111548. Brann, M. R. 1998. Identification of ligands by selective amplification of cells transfected with receptors and marker enzymes.

Cherkasov, et al. 1985. Organothiophosphorus reagents in organic synthesis. *Tetrahedron*, 41(13):2567-2624.

Clark et al. 1983. Antihypertensive 9-substituted 1-Oxa-4,9-diazaspiro[5.5]undecan-3-ones. *J. Med. Chem.*, 26:855-861.

Clifton, et al. 1982. Arylethanolamines Derived from Salicyclamide with a- and b-Adrenoceptor Blocking Activities. Preparation of Labetalol, its Enantiomers, and Related Salicyclamides. *J. Med. Chem.*, 25:670-679.

DeClerck, et al. 1987. Increase in slow-wave sleep in humans with the serotonin-$S_2$ antagonist ritanserin. *Current Therapeutic Research*, 41(4):427-432.

Delecluse, et al. 1998. A case of tardive tremor successfully treated with clozapine. *Movement Disorders*, 13(5):846-847.

Dorwald, F.Z., "Side Reactions in Organic Synthesis: A Guide to Successful Synthesis Design" 2005 Wiley-VCH GmbH & KGaA, Wienheim.

Dunn, et al. 1986. Analgetic and antiinflammatory 7-aroylbenzofuran-5-ylacetic acids and 7-aroylbenzothiophene-5-ylacetic acids. *J. Med. Chem.*, 29:2326-2329.

Durif, et al. 1997. Low-dose clozapine improves dyskinesias in Parkinson's disease. *Neurology*, 48:658-662.

Eichelbaum, et al. 1996. Influence of pharmacogenetics on drug disposition and response. *Clinical and Experimental Pharmacology and Physiology*, 23:983-985.

Emerson, et al. 1938. The reductive alkylation of aniline. *J. Am. Chem. Soc.*, 60:2023-2025.

Ermakov, et al. 1981. Use of Mass spectrometry in structural and stereochemical studies. *Chemistry of Heterocyclic Compounds*, 1:72-77.

Everett, et al. 1970. L-Dopa: Effect on concentrations of dopamine, norepinephrine, and serotonin in brains of mice. *Science*, 168:849-850.

Factor, et al. 1992. Clozapine prevents recurrence of psychosis in Parkinson's disease. *Movement Disorders*, 7(2):125-131.

Factor, et al. 2001. Clozapine for the treatment of drug-induced psychosis in Parkinson's disease: Results of the 12 week open label extension in the PSYCLOPS trial. *Movement Disorders*, 16(1):135-139.

Finar, et al. 1954. The preparation and properties of some derivatives of 1-phenylpyrazole, *J. Chem. Soc.*, pp. 2293-2298.

Fisera, et al. 1994. Synthesis of spiro-substituted 1,3-oxazines by a new sequence leading to spiroheterocycles. *Monatshefte Für Chemie*, 125:909-919.

Friedman, J. II. 1994. Clozapine treatment of psychosis in patients with tardive dystonia: Report of three cases. *Movement Disorders*, 9(3):321-324.

Friedman, et al. 1999. Low-dose clozapine for the treatment of drug-induced psychosis in Parkinson's disease. *N. Engl. J. Med.*, 340(10):757-763.

Friedman, et al. 2000. Atypical antipsychotics in the treatment of drug-induced psychosis in Parkinson's disease. *Movement Disorders*, 15(2):201-211.

Fuller, R. W. 1982. Drugs acting on serotonergic neuronal systems. In N. N. Osborne (Ed.). *Biology of Serotonergic Transmission*. Chap. 9, pp. 221-247. New York: Wiley.

Gainetdinov, et al. 2001. Genetic animal models: Focus on schizophrenia. *Trends in Neurosciences*, 24(9)527-533.

Gamma, et al. 2000. 3,4-Methylenedioxymethamphetamine (MDMA) modulates cortical and limbic brain activity as measured by $[H_2^{15}O]$-PET in healthy humans. *Neuropsychopharmacology*, 23(4):388-395.

Gawley, R. E., & Aubé, J. 1996. *Principles of Asymmetric Synthesis*. New York: Pergamon.

Gershon, M. D., Mawe, G. M., & Branchek, T. A. 1989. 5-Hydroxytryptamine and enteric neurones. In J. R. Fozard (Ed.), *The Peripheral Actions of 5-Hydroxytryptamine* (pp. 247-273). New York: Oxford University Press.

Gillman, P. K. 2005. Monoamine oxidase inhibitors, opioid analgesics and serotonin toxicity. *British Journal of Anaesthesia*, 95(4):434-441.

Glennon, R. A. 1990. Serotonin receptors: Clinical implications. *Neuroscience & Biobehavioral Reviews*, 14:35-47.

Gooβen, et al. 2001. Palladium-catalyzed synthesis of aryl ketones from boronic acids and carboxylic acids or anhydrides. *Angew. Chem. Int. Ed.*, 40:3458-3460.

Gstach et al. 1990. Rearrangement of 3,3-disubstituted 1-aryl-4,5-dihydro-5-oxo-3H-1,2,4-triazolium tetrafluoroborates: Part 1. A versatile synthesis of 1,5-disubstituted 2-aryl-1,2-dihydro-3H-1,2,4-triazol-3-one tetrafluoroborates. *Synthesis*, pp. 803-808.

Guthrie, et al. 1993. The tetrahedral intermediate from the hydration of N-methylformanilide. *Can. J. Chem.*, 71:2109-2122.

Harper, et al. 1964. The chemistry and pharmacology of some 4-aminopiperidines and their derivatives. *J. Med Chem.*, 44:729-732.

Hartwig, J. F. 1998. Transition metal catalyzed synthesis of arylamines and aryl ethers from aryl halides and triflates: Scope and mechanism. *Angew. Chem. Int. Ed.*, 37:2047-2067.

Herrick-Davis, et al. 2000. Inverse agonist activity of atypical antipsychotic drugs at human 5-hydroxytryptamine2C receptors. *The Journal of Pharmacology and Experimental Therapeutics*, 295(1):226-232.

Hickinbottom, W. J. 1930. The preparation of secondary alkylarylamines and their purification. *J. Chem. Soc.*, pp. 992-994.

Hirst, et al. 1895. A method for preparing the formyl derivatives of the aromatic amines. *J. Chem. Soc.*, 67:829-831.

Idzikowski, et al. 1991. A dose response study examining the effects of ritanserin on human slow wave sleep. *Br. J. Clin. Pharmac.*, 31:193-196.

Irikura et al., 1971 "New Anticulcer Agents. 1. Synthesis and Biological Activities of 1-Acyl-2-,-3-, -4-substituted Benzamidopiperdines" *J. Medicinal Chemistry* 14(4): 357-361.

Jaeger, et al. 1941. Two ketones of the stilboestrol group. *J. Chem. Soc.*, 744-747.

Julius, et al. 1990. The 5HT2 receptor defines a family of structurally distinct but functionally conserved serotonin receptors. *Proc. Natl. Acad. Sci. USA*, 87:928-932.

Kalgutkar, et al. 1995. Selective inhibitors of monoamine oxidase (MAO-A and MAO-B) as probes of its catalytic site and mechanism. *Medicinal Research Reviews*, 15(4)325-388. XP002034298.

Kanayama, et al. 2005. New treatment of lumbar disc herniation involving 5-hydroxytryptamine$_{2A}$ receptor inhibitor: A randomized controlled trial. *J. Neurosurg: Spine*, 2:441-446.

Klapars, et al. 2001. A general and efficient copper catalyst for the amidation of aryl halides and the N-arylation of nitrogen heterocycles. *J. Am. Chem. Soc.*, 123:7727-7729.

Klapars, et al. 2002. A general and efficient copper catalyst for the amidation of aryl halides. *J. Am. Chem. Soc.*, 124:7421-7428.

Kuehne, et al. 1991(a). Enantioselective syntheses of vinblastine, leurosidine, vincovaline, and 20'-epi-vincovaline. *J. Org. Chem.*, 56(2):513-528.

Kuehne, et al. 1991(b). Total syntheses of *Yohimbe* alkaloids, with stereoselection for the normal, allo, and 3-epiallo series, based on annelations of 4-methoxy-1,2-dihydropyridones. *J. Org. Chem.*, 56(8):2701-2712.

Kwong, et al. 2002(a). Copper-catalyzed coupling of alkylamines and aryl iodides: An efficient system even in an air atmosphere. *Organic Letters*, 4(4):581-584.

Kwong, et al. 2002(b). A general, efficient, and inexpensive catalyst system for the coupling of aryl iodides and thiols. *Organic Letters*, 4(20):3517-3520.

Kwong, et al. 2003. Mild and efficient copper-catalyzed amination of aryl bromides and primary alkylamines. *Organic Letters*, 5(6):793-796.

Landini, et al. 1974. A convenient synthesis of primary and secondary dialkyl and aryl alkyl sulfides in the presence of phase-transfer catalysts. *Synthesis*, pp. 565-566.

Landolt, et al. 1999. Serotonin-2 receptors and human sleep: Effect of a selective antagonist on EEG power spectra. *Neuropsychopharmacology*, 21(3):455-466.

Leysen, et al. 1978. Serotonergic component of neuroleptic receptors. *Nature*, 272:168-171.

Li, G. Y. 2002. Highly active, air-stable palladium catalysts for the C-C and C-S bond-forming reactions of vinyl and aryl cholrides: Use of commercially available $[(t\text{-Bu})_2P(OH)]_2PdCl_2$,

[(*t*-Bu)₂P(OH)PdCl₂]₂ and [[(*t*-Bu)₂ PO . . . H . . . OP(*t*-Bu)₂]PdCl]₂ as catalysts. *J. Org. Chem.*, 67:3643-3650.

Liechti, et al. 2001. Effects of MDMA (ecstasy) on prepulse inhibition and habituation of startle in humans after pretreament with Citalopram, Haloperidol, or Ketanserin. *Neuropsychopharmacology*, 24(3):240-252.

Linder, et al. 1997. Pharmacogenetics: A laboratory tool for optimizing therapeutic efficiency. *Clinical Chemistry*, 43(2):254-266.

Lowe, et al. 1994. Aza-tricyclic substance P antagonists. *J. Med. Chem.*, 37:2831-2840.

Mansbach, et al. 1988. Dopaminergic stimulation disrupts sensorimotor gating in the rat. *Psychopharmacology*, 94:507-514.

March, et al., Journal of Advanced Organic Chemistry: Reactions, Mechanism and Structure, 5th Edition, p. 423, 2001.

Marek, et al. 2003. Synergistic action of 5-$HT_{2A}$ antagonists and selective serotonin reuptake inhibitors in neuropsychiatric disorders. *Neuropsychopharmacology*, 28:402-412.

Marek, et al. 2005. The selective 5-$HT_{2A}$ receptor antagonist MI00907 enhances antidepressant-like behavioral effects of the SSRI fluoxetine. *Neuropsychopharmacology*, 30:2205-2215.

Mavunkel, et al. 1996. Synthesis and characterization of pseudopeptide bradykinin B2 receptor antagonists containing the 1,3,8-triazaspiro[4.5]decan-4-one ring system. *J. Med. Chem.*, 39:3169-3173.

Mayer, et al. 2003. Ritanserin improves sleep quality in narcolepsy. *Pharmacopsychiatry*, 364:150-155.

Meltzer, et al. 1995. Plasma clozapine levels and the treatment of L-DOPA-induced psychosis in Parkinson's disease. *Neuropsychopharmacology*, 12(1):39-45.

Meltzer, H. Y. 1999. The role of serotonin in antipsychotic drug action. *Neuropsychopharmacology*, 21(2S):106S-115S.

Meng, et al. 1991. Synthetic approaches toward glidobamine, the core structure of the glidobactin antibiotics. *Tetrahedron*, 47(32):62510-6264.

Micovic, et al. 1991. A simple method for preparation of secondary aromatic amines. *Synthesis*, 11:1043-1045.

Miyata, et al. 2000. Sarpogrelate, a selective 5-$HT_{2A}$ serotonergic receptor antagonist, inhibits serotonin-induced coronary artery spasm in a porcine model. *Journal of Cardiovascular Pharmacology*, 35(2) 294-301.

Möehrle, et al. 1990. Sodium mercury edetate dehydrogenation of N-aliphatic substituted 1,2,3,6-tetrahydropyridine derivatives. *Arch. Pharm. (Weinheim)*, 323:109-115.

Moulignier, A. 1994. Récepteurs centraux de la sérotonine principaux aspects fondamentaux et fonctionnels application thérapeutiques. *Rev. Neurol.*, 150:3-15.

Moulignier, A. 1994. Récepteurs centraux de la sérotonine principaux aspects fondamentaux et fonctionnels application thérapeutiques. *Rev. Neurol.*, 150:3-15.

Moune, et al. 1997. Total synthesis of dolatrienoic acid: A subunit of dolastatin 14. *J. Org. Chem.*, 62:3332-3339.

Mullen et al. 2000. (-)-Spiro[1-azabicyclo[2.2.2]octane-3,5'-oxazolidin-2'one], a conformationally restricted analogue of acetylcholine, is a highly selective full agonist at the α7 nicotinic acetylcholine receptor. *J. Med. Chem.*, 43:4045-4050.

Muri, et al. 1998. Synthesis of new benzylic ethers of oximes derived from 1-phenyl-pyrazole compounds. *Synthetic Communications*, 28(7):1299-1321.

Ng, et al. 1970. L-dopa-induced release of cerebral monoamines. *Science*, 170:76-77.

Nigam, et al. 1957a. Studies with acetylenes. Part II. Some reactions of Grignard reagents with propargylie halides. Model linoleic and linolenic acid systems. *J. Chem Soc.*, pp. 3868-3873.

Nigam, et al. 1957b. The conversion of fatty acids into aldehydes. *J. Chem. Soc.*, pp. 3320-3321.

Nordstrom, et al. 1993. High 5-$HT_2$ receptor occupancy in clozapine treated patients demonstrated by PET. *Psychopharmacology*, 110:365-367.

Ogawa, et al. 2005. Effects of R-102444 and its active metabolite R-96544, selective 5-HT2A receptor antagonists, on experimental acute and chronic pancreatitis: Additional evidence for possible involvement of 5-HT2A receptors in the development of experimental pancreatitis. European Journal of Pharmacology, 521:156-163.

Olah, et al. 1956. Notiz über die *n*-formylierung von aminen mit formylfluorid. *Chem. Ber.*, 89:2211-2212.

Old, et al. 2002. Efficient palladium-catalyzed *n*-arylation of indoles. *Organic Letters*, 2(10):1403-1406.

Pace, et al. 1991. A mutant a subunit of $G_{i2}$ induces neoplastic transformation of Rat-1 cells. *Proc. Natl. Acad. Sci. USA*, vol. 88:7031-7035.

Paiva, et al. 1988. Effects of ritanserin on sleep disturbances of dysthymic patients. *Psychopharmacology*, 96:395-399.

Patel, et al. 2004. The highly selective 5-hydroxytryptamine (5-$HT)_{2A}$ receptor antagonist, EMD 281014, significantly increases swimming and decreases immobility in male congenital learned helpless rats in the forced swim test. *Synapse*, 52:73-75.

Pierce, et al. 1995. 5-hydroxytryptamine-induced synovial plasma extravasation is mediated via 5-hydroxytryptamine2A receptors on sympathetic efferent terminals. *The Journal of Pharmacology and Experimental Therapeutics*, 275(1):502-508.

Pollak, et al. 1999. Clozapine in drug-induced psychosis in Parkinson's disease. *The Lancet*, 353:2041-2042.

R&D Focus Drug News, vol. 10(44): 1-4 (Nov. 12, 2001).

Read, W. T. 1922. Researches on hydantoins. Synthesis of the soporific, 4,4-phenylethyl-hydantoin(nirvanol). *J. Am. Chem. Soc.*, 44:1746-1755.

Ricci, A. 2000. *Modern Amination Methods*. New York: Wiley-VCH.

Rice, et al. 1955. Raney nickel catalyzed n-alkylation of aniline and benzidine with alcohols. *J. Am. Chem. Soc.*, 77:4052-4054.

Roberts. C., 2006, "Drug Evaluation: ACP-103, a 5-HT2A Receptor Inverse Agonist," Current Opinion InvestiRative DruRs, vol. 7(7);653-660.

Rubiralta, M., Giralt, E., & Diez, A. 1991. *Studies in Organic Chemistry 43. Piperidine: Structure, Preparation, Reactivity and Synthetic Applications of Piperidine and its Derivatives*. New York: Elsevier.

Ryckmans, et al. 2002. First dual Nk1 antagonists—serotonin reuptake inhibitors: synthesis and SAR of a new class of potential antidepressants. *Biorganic & Medicinal Chemistry Letters* 12:261-264.

Sadzot, et al. 1989. Hallucinogenic drug interactions at human brain 5-$HT_2$ receptors: Implications for treating LSD-induced hallucinogenesis. *Psychopharmacology*, 98:495-499.

Saltzman, et al. 1991. Cloning of the human serotonin 5-HT2 and 5-HT1C receptor subtypes. *Biochemical and Biophysical Research Communications*, 181(3):1469-1478.

Saxena, et al. 1990. Cardiovascular effects of serotonin agonists and antagonists. *Journal of Cardiovascular Pharmacology*, 15(Supp. 7):S17-S34.

Scheibye, et al. 1978. Studies on organophosphorus compounds XXI. The dimer of *p*-methoxyphenylthionphosphine sulfide as thiation reagent. A new route to thiocarboxamides. *Bull. Soc. Chim. Belg.*, 87:229-238.

Schins, et al. 2003. Increased coronary events in depressed cardiovascular patients: 5-$HT_{2A}$ receptor as missing link? *Psychosomatic Medicine*, 65:729-737.

Screttas, et al. 1978. Hydrolithiation of α-olefins by a regiospecific two-step process. Transformation of alkyl phenyl sulfides to alkyllithium reagents. *J. Org. Chem.*, 43(6):1064-1071.

Sharpley, et al. 1994. Slow wave sleep in humans: Role of 5-$HT_{2A}$ and 5-$HT_{2C}$ receptors. *Neuropharmacology*, 33(3/4):467-471.

Smith, et al. 1995. New spiropiperdines as potent and selective nonpeptide tachykinin $NK_2$ receptor antagonists. *J. Med. Chem.*, 38(19):3772-3779.

Stefancich, et al. 1984. Agenti antiinfiammatori non-steroidci: Nota III—sintesi ed attività analgesica-antiinfiammatoria di 4-(pirrol-1-il)-fenilacetamidi e di 4-(pirrol-1-il)fenetilamine. *Farmaco Ed. Sci.*, 39(9):752-764.

Stryjer, et al. 2003. Treatment of neuroleptic-induced akathisia with the 5-$HT_{2A}$ antagonist trazodone. *Clinical Neuropharmacology*, 26(3):137-141.

Thomas, et al. 1997. "Rapid in-plate generation of benzimidazole libraries and amide formation using EEDQ." *Tetrahedron Lett.* 39(29):5099-5102.

Tolstikov et al.1991 "Synthesis and Reactivity of N-substituted aminoamides, antiarrhythmic and local anaesthetic activity" *Russian Chemical Reviews* 60(4):420434.

Tsukamoto, et al. 1995. Synthesis and structure-activity studies of a series of 1-oxa-2,8-diazaspiro[4.5]decan-3-ones and related compounds as $M_1$ muscarinic agonists. *Chem. Pharm. Bull.*, 43(9):1523-1529.

Vallar, et al. 1987. Altered $G_S$ and adenylate cyclase activity in human GH-secreting pituitary adenomas. *Nature*, 330:566-568.

Van Laar, et al. 2001. Subchronic effects of the GABA-agonist lorazepam and the 5-$HT_{2A/2C}$ antagonist ritanserin on driving performance, slow wave sleep and daytime sleepiness in healthy volunteers. *Psychopharmacology*, 154:189-197.

Vanover et al., 2003, "ACP-IIB, A 5-HT1A Receptor Inverse Agonist, A Novel Potential Treatment for Psychosis," Schizovhrenia Research, vol. 60, No. I , SuPP. rS1, p. 317.

Vanover et al., 2006, "Pharmacological and Behavioral Profile of N-(4-fluorophenylmethyl)-N-( 1-mcthylpiperidin' 4-y 1)-N'-(4-(2-methylpropyloxy)phenylmethyl) Carbamide (2R. 3R)-Dihydroxybutanedioate (2:1) (ACP-103), a Novel 5-Hydroxytrptamine 2A Receptor Inverse Agonist," J. *Pharmacology & Experimental Therapeutics*, vol. 317(2):910-918.

Varma, et al. 1999. Microwave-accelerated solvent-free synthesis of thioketones, thiolactones, thioamides, thionoesters, and thioflavonoids. *Organic Letters*, 1(5):697-700.

Viola, et al. 2002. Ritanserin, a serotonin-2 receptor antagonist, improves ultradian sleep rhythmicity in young poor sleepers. *Clinical Neurophysiology*, 113:429-434.

Vogel, A. I. 1948. Physical properties and chemical constitution. Part XIX. Five-membered and six-membered carbon rings. *J. Chem. Soc.*, pp. 1809-1813.

Vogl, et al. 2002. Palladium-catalyzed monoarylation of nitroalkanes. *J. Org. Chem.*, 67(1):106-111.

Wade, et al. 2000. Application of base cleavable safety catch linkers to solid phase library production. *J. Comb. Chem.*, 2(3):266-275.

Weiner, et al. 2001. 5-Hydroxytryptamine$_{2A}$ receptor inverse agonists as antipsychotics. *The Journal of Pharmacology and Experimental Therapeutics*, 299(1):268-276.

Whitmore, et al. 1942. Abnormal Grignard reactions. XII. Sterically hindered aliphatic carbonyl compounds. II. Ketones containing the dineopentylcarbinyl group. *J. Am. Chem. Soc.*, 64:1247-1251.

Whitmore, et al. 1947. Higher hydrocarbons. IV. Six phenyleicosanes and six cyclohexyleicosanes. *J. Am. Chem. Soc.*, 69:235-237.

Wolf, V. V. 1952. Über alkin-amine I. Aryl-propargyl-amine. *Liebigs Ann. Chem.*, 576:35-45.

Wolfe, et al. 1996. An improved catalyst system for aromatic carbon-nitrogen bond formation: The possible involvement of his(phosphine) palladium complexes as key intermediates. *J. Am. Chem. Soc.*, 118:7215-7216.

Yamada, et al. 1998. Alternative synthesis of TTF donors with a dioxolane ring, and synthesis of their dithiolane and oxathiolane analogues. *Tetrahedron Letters*, 39:7709-7712.

Yang, et al. 1999. Palladium-catalyzed amination of aryl halides and sulfonates. *Journal of Organometallic Chemistry*, 576:125-146.

Yasuhara, et al. 2000. An activated phosphate for an efficient amide and peptide coupling reagent. *J. Chem. Soc., Perkin Trans. I*, 17:2901-2902.

Yin, et al. 2002. Pd-catalyzed intermolecular amidation of aryl halides: The discovery that xantphos can be trans-chelating in a palladium complex. *J. Am. Chem. Soc.*, 124:6043-6048.

Yoshida, et al. 1998. Marked improvement of tardive dystonia after replacing haloperidol with risperidone in a schizophrenic patient. *Clinical Neuropharmacology*, 21(1):68-69.

Lian Yu, Professor, School of Pharmacy, University of Wisconsin-Madison-webpage-http://www.pharmacy.wisc.edu/SOPDir/PersonDetails.efm?ID=32, Aug. 24, 2009.

Notice of Allowance and Fee(s) Due and Notice of Allowability dated May 15, 1997, from U.S. Appl. No. 08/273,669, filed Jul. 12, 1994, now U.S. Pat. No. 5,707,798.

Office Action dated Mar. 27, 1998, from U.S. Appl. No. 08/954,724, filed Oct. 20, 1997, now U.S. Pat. No. 5,912,132.

Notice of Allowance and Fee(s) Due and Notice of Allowability dated Sep. 4, 1998, from U.S. Appl. No. 08/954,724, filed Oct. 20, 1997, now U.S. Pat. No. 5,912,132.

Office Action dated Sep. 14, 1998, from U.S. Appl. No. 08/965,947, filed Nov. 7, 1997, now U.S. Pat. No. 5,955,281.

Interview Summary dated Nov. 17, 1998, from U.S. Appl. No. 08/965,947, filed Nov. 7, 1997, now U.S. Pat. No. 5,955,281.

Office Action dated Apr. 25, 2002, from U.S. Appl. No. 09/800,096, now U.S. Pat. No. 6,815,458.

Office Action dated Jan. 21, 2003, from U.S. Appl. No. 09/800,096, now U.S. Pat. No. 6,815,458.

Office Action dated Jul. 15, 2003, from U.S. Appl. No. 09/800,096, now U.S. Pat. No. 6,815,458.

Notice of Allowability dated Dec. 8, 2003, from U.S. Appl. No. 09/800,096, filed Mar. 6, 2001, now U.S. Pat. No. 6,815,458.

Notice of Allowance and Fee(s) Due and Notice of Allowability dated Dec. 5, 2003, from U.S. Appl. No. 10/409,782, filed Apr. 7, 2003, now U.S. Pat. No. 6,756,393.

International Preliminary Examination Report dated Mar. 18, 2003, for PCT/US01/07187.

International Search Report dated Jul. 17, 2001 for PCT/US01/07187.

Written Opinion dated Nov. 22, 2002 for PCT/US01/07187.

Office Action dated Feb. 28, 2001, from U.S. Appl. No. 09/413,626, filed Oct. 6, 1999, now U.S. Pat. No. 6,358,698.

Notice of Allowance and Fee(s) Due and Notice of Allowability dated Nov. 20, 2001, from U.S. Appl. No. 09/413,626, filed Oct. 6, 1999, now U.S. Pat. No. 6,358,698.

Office Action dated May 21, 2004, from U.S. Appl. No. 10/329,719, filed Dec. 23, 2002, now U.S. Pat. No. 6,911,452.

Notice of Allowance and Fee(s) Due and Notice of Allowability dated Feb. 11, 2005, from U.S. Appl. No. 10/329,719, filed Dec. 23, 2002, now U.S. Pat. No. 6,911,452.

Office Action dated Jan. 17, 2006, from U.S. Appl. No. 11/154,083, filed Jun. 26, 2005.

Office Action dated Jun. 26, 2006, from U.S. Appl. No. 11/154,083, filed Jun. 26, 2005.

Notice of Allowability, Notice of Allowance and Fee(s) Due, and Interview Summary dated Dec. 15. 2006, from U.S. Appl. No. 11/154,083, filed Jun. 16, 2005.

Office Action dated Oct. 5. 2006, from U.S. Appl. No. 11/418,322, filed May 3, 2006.

Office Action dated Jan. 23, 2007, from U.S. Appl. No. 11/418,322, filed May 3, 2006.

International Search Report dated May 8, 2003 for PCT/US02/41476.

Written Opinion dated Sep. 9, 2003, for PCT/US02/41476.

International Preliminary Examination Report dated Jan. 15, 2004, fpr PCT/US02/41476.

Office Action dated Nov. 4, 2004, from U.S. Appl. No. 10/601,070, filed Jun. 20, 2003.

Notice of Allowance and Fee(s) Due and Notice of Allowability dated Jul. 12, 2005, from U.S. Appl. No. 10/601,070, filed Jun. 20, 2003.

Notice of Allowance and Fee(s) Due and Notice of Allowability dated Mar. 29, 2006, from U.S. Appl. No. 10/601,070, filed Jun. 20, 2003.

International Search Report dated Dec. 3, 2003, for PCT/US03/19797.

Written Opinion for PCT/US03/19797 dated Apr. 5, 2004.

International Preliminary Examination Report dated Jul. 28, 2004 for PCT/US03/19797.

International Search Report dated Sep. 8, 2004, for PCT/US2004/001234.

International Written Opinion dated Sep. 8, 2004, for PCT/US2004/001234.

International Preliminary Report on Patentability dated Apr. 14, 2005, for PCT/US2004/001234.

International Search Report dated Jan. 30, 2006, for PCT/US2005/034813.

Written Opinion of the International Searching Authority dated Jan. 30, 2006, for PCT/US2005/034813.

International Search Report dated Jan. 30, 2006, for PCT/US2005/034376.

Written Opinion of the International Searching Authority dated Jan. 30, 2006, for PCT/US2005/034376.

International Preliminary Report on Patentability dated Mar. 27, 2007, for PCT/US2005/034376.

International Preliminary Report on Patentability dated Mar. 27, 2007, for PCT/US2005/034813.

Office Action dated Apr. 6, 2007, from U.S. Appl. No. 11/418,322, filed May 3, 2006.
Office Action dated May 8, 2007, from U.S. Appl. No. 11/417,866, filed May 3, 2006.
Notice of Allowance and Fee(s) Due and Notice of Allowability dated Mar. 5, 2007, from U.S. Appl. No. 10/601,070, filed Jun. 20, 2003.
Office Action dated Feb. 5, 2007, from U.S. Appl. No. 11/299,566, filed Dec. 12, 2005.
Notice of Allowance and Fee(s) Due and Notice of Allowability dated Jun. 19, 2007, from U.S. Appl. No. 11/418,322, filed May 3, 2006.
Office Action dated Oct. 22, 2007 from U.S. Appl. No. 11/417,782, filed May 3, 2006.
Office Action dated Oct. 12, 2007 from U.S. Appl. No. 11/417,439, filed May 3, 2006.
Office Action dated Oct. 2, 2007, from U.S. Appl. No. 11/299,566, filed Dec. 12, 2005.
Office Action dated Oct. 26, 2007, from U.S. Appl. No. 11/417,866, filed May 3, 2006.
Office Action dated Oct. 10, 2007, from U.S. Appl. No. 10/759,561, filed Jan. 15, 2004.
Office Action dated Jul. 11, 2008, from U.S. Appl. No. 10/759,561, filed Jan. 15, 2004.
Office Action dated Jan. 6. 2009, from U.S. Appl. No. 10/759,561, filed Jan. 15, 2004.
Notice of Allowance and Fee(s) Due and Notice of Allowability dated Jun. 17, 2009, from U.S. Appl. No. 10/759,561.
Office Action dated Jan. 30, 2008, from U.S. Appl. No. 11/417,790, filed May 3, 2006.
Office Action dated Jan. 25, 2008, from U.S. Appl. No. 10/802,970, filed Mar. 16, 2004.
Notice of Allowance and Fee(s) Due and Notice of Allowability dated Feb. 19, 2008, from U.S. Appl. No. 11/417,439, filed May 3, 2006.
Office Action dated Dec. 17. 2007, from U.S. Appl. No. 11/299,566, filed Dec. 12, 2005.
Office Action dated Feb. 22, 2008, from U.S. Appl. No. 11,417,866, filed May 3, 2006.
Office Action dated Mar. 28. 2008, from U.S. Appl. No. 11/417,782, filed May 3, 2006.
Office Action dated Jul. 14, 2006, from U.S. Appl. No. 10/601,070, filed Jun. 20, 2003.
Supplemental Notice of Allowability dated May 23, 2008, from U.S. Appl. No. 11/417,439, filed May 3, 2006.
Office Action dated Jun. 2, 2008, from U.S. Appl. No. 11/687,552, filed Mar. 16, 2007.
Office Action dated Jul. 17, 2008, from U.S. Appl. No. 10/802,970, filed Mar. 16, 2004.
Notice of Allowance and Fee(s) Due and Notice of Allowability dated Jul. 23, 2008, from U.S. Appl. No. 11/299,566, filed Dec. 12, 2005.

SYNTHESIS OF N-(4-FLUOROBENZYL)-N-(1-METHYLPIPERIDIN-4-YL)-N'-(4-(2-METHYLPROPYLOXY)PHENYLMETHYL)CARBAMIDE AND ITS TARTRATE SALT AND CRYSTALLINE FORMS

CROSS-REFERENCE TO RELATED APPLICATIONS

This application is a continuation of U.S. application Ser. No. 11/235,558, filed on Sep. 26, 2005 now U.S. Pat. No. 7,732,615, which is a non-provisional of U.S. Provisional Application No. 60/614,014, filed on Sep. 27, 2004, entitled "SYNTHESIS OF N-(4-FLUOROBENZYL) -N-(1-METHYLPIPERIDIN-4-YL)-N'-(4-(2-METHYLPROPYLOXY) PHENYLMETHYL)CARBAMIDE AND ITS TARTRATE SALT AND CRYSTALLINE FORMS," each of which is incorporated by reference in its entirety.

BACKGROUND OF THE INVENTION

1. Field of the Invention

The present invention relates to the fields of medicine and chemistry. More particularly, the present invention relates to N-(4-fluorobenzyl)-N-(1-methylpiperidin-4-yl)-N'-(4-(2-methylpropyloxy)-phenylmethyl)carbamide, its tartrate salt, and polymorphs and syntheses and uses thereof.

2. Description of the Related Art

WO 01/66521 describes N-azacycloalkyl-N-aralkyl carbamides and carboxylic acid amides, which constitute a new class of compounds effective in inhibiting an activity of monoamine receptors, including the serotonin receptor of the 5-HT2A subclass. WO 01/66521 is incorporated herein by reference in its entirety. Examples of disease conditions for which such compounds can be used include, but are not limited to, neuropsychiatric diseases such as schizophrenia and related idiopathic psychoses, depression, anxiety, sleep disorders, appetite disorders, affective disorders such as major depressions, bipolar disorder, depression with psychotic features and Tourette's Syndrome. Other beneficial treatments may be drug-induced psychoses and side-effects of Parkinson's disease as well as psychoses secondary to neurodegenerative disorders such as Alzheimer's or Hunting-ton's Disease, hypertension, migraine, vasospasm, ischemia and the primary treatment and secondary prevention of various thrombotic conditions including myocardial infarction, thrombotic or ischemic stroke, idiopathic and thrombotic thrombocytopenic purpura and peripheral vascular disease.

SUMMARY OF THE INVENTION

One embodiment disclosed herein includes a method for the preparation of a compound of formula I:

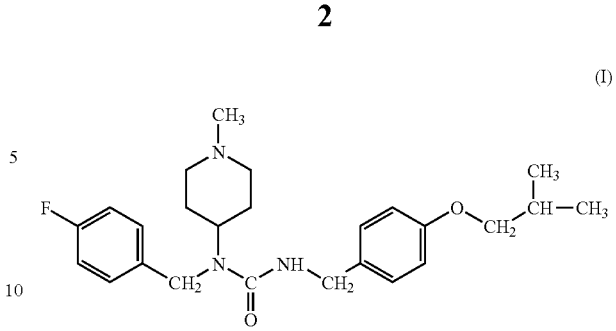

that includes reacting (4-fluorobenzyl)-(1-methylpiperidin-4-yl)amine of formula II (II)

with 4-(2-methylpropyloxy)phenylmethyl-isocyanate of formula III (III)

In some embodiments, about 0.9 to about 1.1 equivalents of the (4-fluorobenzyl)-(1-methylpiperidin-4-yl)amine is used per equivalent of the 4-(2-methylpropyloxy)phenylmethyl-isocyanate. Some embodiments further include isolating the compound of formula I after the reacting. In some embodiments, the isolating includes adding a salt-forming acid after the reacting, isolating the formed salt by solvent removal, precipitation, or both solvent removal and precipitation, adding the isolated salt to a two phase system comprising an organic solvent phase and an alkaline aqueous phase, and obtaining the compound of formula I from the organic solvent phase. In some embodiments, the salt forming acid is selected from the group consisting of one or more of the following: mineral acids, mono- or dicarboxylic acids, and sulfonic acids. In some embodiments, the pH of the aqueous phase is greater than about 8.5. In one embodiment this pH is obtained by adding an aqueous alkaline metal hydroxide. In some embodiments, the reaction is carried out in the presence of an inert organic solvent. In some embodiments, the solvent is selected from the group consisting of one or more of the following: aliphatic ethers, esters of aliphatic carboxylic acids, alcohols, lactones, halogenated hydrocarbons, and aliphatic $C_3$-$C_8$ ketones. In some embodiments, the reaction is carried out at a temperature from about −30° C. to about 60° C.

Another embodiment disclosed herein includes a crystalline form of N-(4-fluorobenzyl)-N-(1-methylpiperidin-4-yl)-N'-(4-(2-methylpropyloxy)phenylmethyl)carbamide that exhibits a melting point of about 124° C., determined with Differential Scanning Calorimetry (DSC) at a heating rate of 10° C./minute.

Another embodiment disclosed herein includes a crystalline form of N-(4-fluorobenzyl)-N-(1-methylpiperidin-4-yl)-N'-(4-(2-methylpropyloxy)phenylmethyl)carbamide that exhibits a X-ray powder diffraction pattern comprising peaks having d-values in angstroms of about 13.0, about 10.9, about 6.5, about 4.7, about 4.3, about 4.22, and about 4.00. In one embodiment, the crystalline form exhibits a X-ray powder diffraction pattern comprising peaks having d-values in angstroms of about 13.0, about 10.9, about 6.8, about 6.5, about 6.2, about 5.2, about 4.7, about 4.5, about 4.3, about 4.22, about 4.00, about 3.53, about 3.40, about 3.28, about 3.24, about 3.19, about 3.08, about 2.91, and about 2.72.

Another embodiment disclosed herein includes a method for the preparation of the above crystalline form including dissolving a salt of a compound of formula I in water:

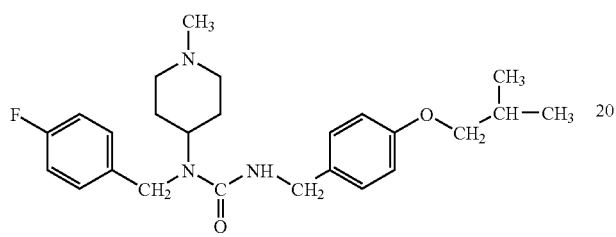

(I)

adding an amount of an organic aprotic solvent to the aqueous salt solution sufficient to dissolve the compound of formula I;

adjusting the pH of the aqueous salt solution to a value of at least about 8.5 by addition of a base;

removing a part of the organic aprotic solvent;

cooling the remaining organic aprotic solution to less than 15° C.; and isolating any precipitate formed.

In some embodiments, the salt of the compound of formula I is a hemitartrate salt. Some embodiments further include extracting the aqueous solution with the organic solvent and collecting all organic phases prior to removing a part of the organic solvent. In one embodiment, the organic solvent is selected from the group consisting of one or more of the following: hydrocarbons, halogenated hydrocarbons, esters of aliphatic carboxylic acids, alcohols, lactones, ethers, and aliphatic $C_4$-$C_8$ ketones.

Another embodiment disclosed herein includes a crystalline form of N-(4-fluorobenzyl)-N-(1-methylpiperidin-4-yl)-N'-(4-(2-methylpropyloxy)phenylmethyl) carbamide produced by the process that includes dissolving a hemi-tartrate salt of a compound of formula I in water:

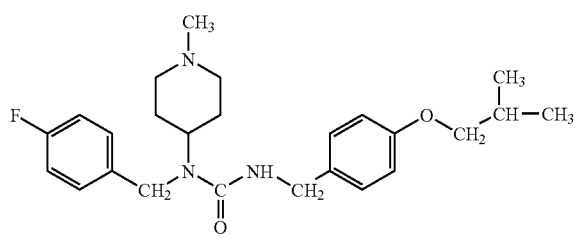

(I)

adding an amount of an organic aprotic solvent to the aqueous salt solution sufficient to dissolve the compound of formula I, adjusting the pH of the aqueous salt solution to a value of at least about 8.5 by addition of a base, extracting the aqueous solution with the organic solvent and collecting all organic phases, removing a part of the organic aprotic solvent, cooling the remaining organic aprotic solution to less than 15° C., and isolating any precipitate formed.

Another embodiment disclosed herein is N-(4-fluorobenzyl)-N-(1-methylpiperidin-4-yl)-N'-(4-(2-methylpropyloxy)phenylmethyl)carbamide hemi-tartrate of formula IV,

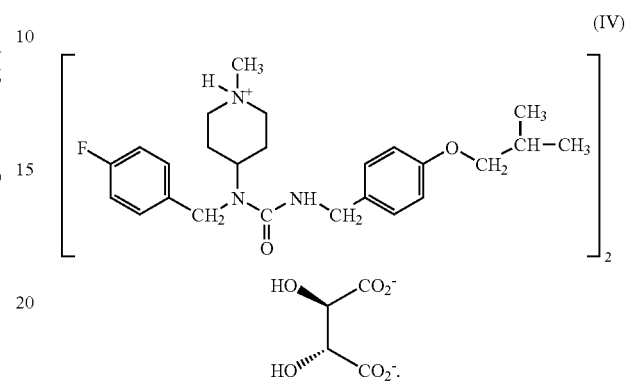

(IV)

Another embodiment disclosed herein includes a method for the preparation of N-(4-fluorobenzyl)-N-(1-methylpiperidin-4-yl)-N'-(4-(2-methylpropyloxy)phenylmethyl)carbamide hemi-tartrate, comprising performing the reaction for synthesizing the compound of formula I as described above, adding tartaric acid after the reaction, and isolating the hemi-tartrate salt formed. In one embodiment, the isolating includes obtaining the hemi-tartrate salt from a suspension formed after addition of tartaric acid. In one embodiment, the isolating includes precipitating the hemi-tartrate salt by cooling, solvent removal, adding a non-solvent, or a combination of these methods.

Another embodiment disclosed herein includes a crystalline form of N-(4-fluorobenzyl)-N-(1-methylpiperidin-4-yl)-N'-(4-(2-methylpropyloxy)phenylmethyl)carbamide hemi-tartrate that exhibits a X-ray powder diffraction pattern comprising peaks having d-values in angstroms of about 18.6, about 16.7, about 10.2, about 6.2, about 6.1, about 4.63, about 4.49, about 4.44, and about 3.96. In one embodiment, the X-ray powder diffraction pattern includes peaks having d-values in angstroms of about 18.6, about 16.7, about 10.2, about 8.2, about 7.7, about 7.4, about 6.5, about 6.2, about 6.1, about 5.86, about 5.14, about 5.03, about 4.78, about 4.69, about 4.63, about 4.49, about 4.44, about 4.35, about 4.10, about 3.96, and about 3.66.

In one embodiment, the above crystalline form is prepared by dissolving the compound of formula IV in ethanol or an admixture of ethanol and isopropanol:

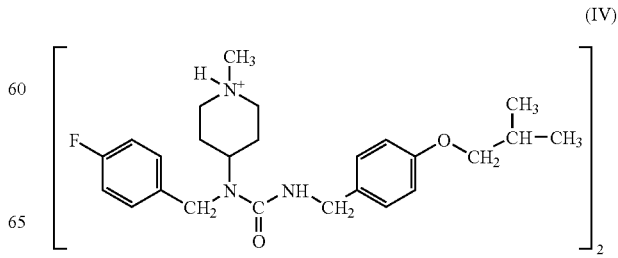

(IV)

-continued

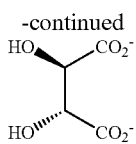

cooling the solution to a temperature of less than about 20° C., and isolating any resulting precipitated solid. In one embodiment, the temperature during the dissolution step is about 55 to about 90° C. In one embodiment, the cooling rate during the cooling step is about 0.1 to about 3° C./minute.

Another embodiment disclosed herein includes a crystalline form of N-(4-fluorobenzyl)-N-(1-methylpiperidin-4-yl)-N'-(4-(2-methylpropyloxy)phenylmethyl) carbamide tartrate produced by a method that includes dissolving the compound of formula IV in ethanol or an admixture of ethanol and isopropanol at a temperature of about 55 to about 90° C.:

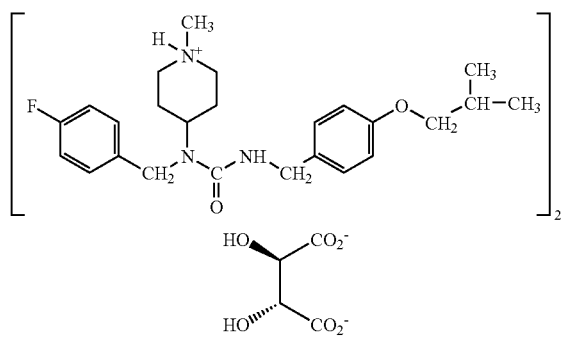

(IV)

cooling the solution to a temperature of less than about 20° C. at a rate of about 0.1 to about 3° C./minute, and isolating any resulting precipitated solid.

Another embodiment disclosed herein includes a crystalline form of N-(4-fluorobenzyl)-N-(1-methylpiperidin-4-yl)-N'-(4-(2-methylpropyloxy)phenylmethyl)carbamide tartrate that exhibits a X-ray powder diffraction pattern comprising peaks having d-values in angstroms of about 17.4, about 10.2, about 5.91, about 4.50, about 4.37, and about 3.87. One embodiment exhibits a X-ray powder diffraction pattern comprising peaks having d-values in angstroms of about 17.4, about 10.2, about 8.8, about 6.4, about 5.91, about 5.46, about 4.99, about 4.90, about 4.62, about 4.50, about 4.37, about 4.20, about 3.87, about 3.73, about 3.58, about 3.42, and about 2.90.

Another embodiment disclosed herein includes a crystalline form of N-(4-fluorobenzyl)-N-(1-methylpiperidin-4-yl)-N'-(4-(2-methylpropyloxy)phenylmethyl) carbamide tartrate that exhibits a X-ray powder diffraction pattern comprising peaks having d-values in angstroms of about 12.0, about 10.7, about 5.86, about 4.84, about 4.70, about 4.57, and about 3.77, hereinafter referred to as Form C. One embodiment exhibits a X-ray powder diffraction pattern comprising peaks having d-values in angstroms of about 12.0, about 10.7, about 7.4, about 6.9, about 6.6, about 6.2, about 5.86, about 5.53, about 5.28, about 5.16, about 4.84, about 4.70, about 4.57, about 4.38, about 4.09, about 3.94, about 3.77, about 3.71, about 3.49, about 3.46, about 3.25, about 3.08, and about 2.93.

Another embodiment disclosed herein includes a method for the preparation of the crystalline form described above that includes suspending of a solid form of a compound of formula IV in an aprotic solvent:

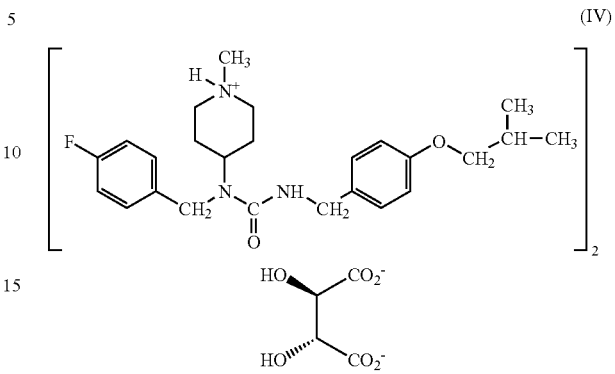

(IV)

and stirring the suspension while adding crystal seeds of crystalline form C, described herein. In one embodiment, the temperature of the solvent during the suspending step is from about 30 to about 100° C. In one embodiment, the aprotic solvent is selected from the group comprising of one or more of the following: aliphatic or cyclic ethers, carboxylic esters, lactones, alkanes, and aliphatic $C_3$-$C_8$ ketones. In one embodiment, the seeding is carried out at a temperature from about 40 to about 80° C. One embodiment further includes cooling the suspension at a rate from about 0.1 to about 1° C./minute. In one embodiment, the suspension is cooled to about room temperature.

Another embodiment disclosed herein includes a method for the preparation of the crystalline form described above that includes suspending a crystalline form of N-(4-fluorobenzyl)-N-(1-methylpiperidin-4-yl)-N'-(4-(2-methylpropyloxy)phenylmethyl) carbamide tartrate or mixtures of crystalline forms of N-(4-fluorobenzyl)-N-(1-methylpiperidin-4-yl)-N'-(4-(2-methylpropyloxy)phenylmethyl)carbamide tartrate in a polar and aprotic solvent at temperatures from about 30 to about 70° C., stirring the suspension while adding crystal seeds of the crystalline form C, described herein, and isolating of the crystalline solid from the suspension.

Another embodiment disclosed herein includes a method for the preparation of the crystalline form described above that includes dissolving a tartrate salt of N-(4-fluorobenzyl)-N-(1-methylpiperidin-4-yl)-N'-(4-(2-methylpropyloxy)phenylmethyl) carbamide in a solvent at temperatures from about 0 to about 70° C., stirring the resulting solution at a temperature of about 50 to about 70° C. while adding crystal seeds of crystalline form C, cooling the obtained suspension at a cooling rate of about 5 to about 15° C. per hour to a temperature of about −20° C. to about room temperature, and isolating crystalline solid from the suspension. In one embodiment, the solvent is tetrahydrofuran. In other embodiments, the solvent is selected from the group consisting of one or more of acetone, ethanol, isopropanol, dichloromethane, 1,4-dioxane, and acetonitrile.

Another embodiment disclosed herein includes a crystalline form of N-(4-fluorobenzyl)-N-(1-methylpiperidin-4-yl)-N'-(4-(2-methylpropyloxy)phenylmethyl)carbamide tartrate produced by a process that includes suspending a crystalline form of N-(4-fluorobenzyl)-N-(1-methylpiperidin-4-yl)-N'-(4-(2-methylpropyloxy)phenylmethyl) carbamide tartrate or mixtures of crystalline forms of N-(4-fluorobenzyl)-N-(1-methylpiperidin-4-yl)-N'-(4-(2-methylpropyloxy)phenylmethyl) carbamide tartrate in a polar and aprotic solvent at temperatures from about 30 to about 70° C., stirring the suspension while adding crystal seeds of the crystalline form C, and isolating of the crystalline solid from the suspension.

Another embodiment disclosed herein includes a crystalline form of N-(4-fluorobenzyl)-N-(1-methylpiperidin-4-yl)-N'-(4-(2-methylpropyloxy)phenylmethyl) carbamide tartrate produced by a process that includes dissolving a tartrate salt of N-(4-fluorobenzyl)-N-(1-methylpiperidin-4-yl)-N'-(4-(2-methylpropyloxy)phenylmethyl) carbamide in tetrahydrofuran or acetone at temperatures from about 0 to about 70° C., stirring the resulting solution at a temperature of about 50 to about 70° C. while adding crystal seeds of the crystalline form C, cooling the obtained suspension at a cooling rate of about 5 to about 15° C. per hour to a temperature of about −20° C. to about room temperature, and isolating crystalline solid from the suspension.

Another embodiment disclosed herein includes a crystalline form of N-(4-fluorobenzyl)-N-(1-methylpiperidin-4-yl)-N'-(4-(2-methylpropyloxy)phenylmethyl) carbamide tartrate including from about 0% to about 6.6% isopropanol or ethanol that exhibits a X-ray powder diffraction pattern comprising peaks having d-values in angstroms of about 17.2, about 16.0, about 6.1, about 4.64, about 4.54, and about 4.37. One embodiment exhibits a X-ray powder diffraction pattern comprising peaks having d-values in angstroms of about 17.2, about 16.0, about 10.7, about 9.8, about 6.6, about 6.1, about 6.00, about 5.73, about 5.33, about 5.17, about 4.91, about 4.64, about 4.54, about 4.37, about 4.10, about 3.91, about 3.84, about 3.67, about 3.55, about 3.42, about 3.32, about 3.13, and about 3.06.

Another embodiment disclosed herein includes a crystalline form of N-(4-fluorobenzyl)-N-(1-methylpiperidin-4-yl)-N'-(4-(2-methylpropyloxy)phenylmethyl) carbamide tartrate comprising about 5% t-butyl methyl ether that exhibits a X-ray powder diffraction pattern comprising peaks having d-values in angstroms of about 17.3, about 16.2, about 10.6, about 9.8, about 8.1, about 7.5, about 6.6, about 6.0, about 5.28, about 5.09, about 4.90, about 4.72, about 4.51, about 4.39, about 4.26, about 4.04, about 3.86, about 3.70, about 3.54, about 3.48, and about 3.02.

Another embodiment disclosed herein includes a crystalline form of N-(4-fluorobenzyl)-N-(1-methylpiperidin-4-yl)-N'-(4-(2-methylpropyloxy)phenylmethyl) carbamide tartrate comprising about 3% of tetrahydrofuran that exhibits a X-ray powder diffraction pattern comprising peaks having d-values in angstroms of about 19.0, about 16.0, about 13.0, about 7.8, about 6.4, about 6.2, about 5.74, about 5.29, about 5.04, about 4.83, about 4.62, about 4.50, about 4.34, about 4.24, about 4.05, about 3.89, about 3.76, about 3.58, and about 3.27.

Another embodiment disclosed herein includes a pharmaceutical composition comprising the compound of formula IV and a pharmaceutically acceptable carrier or diluent:

(IV)

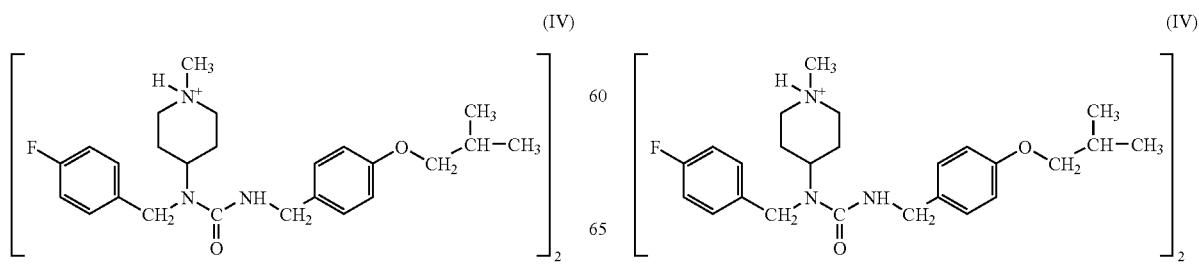

Other embodiments disclosed herein include pharmaceutical compositions that include any of the crystalline forms described above and a pharmaceutically acceptable carrier or diluent.

Another embodiment disclosed herein includes a method of delivering the compound of formula I to a host, comprising administering to a subject a compound of formula IV:

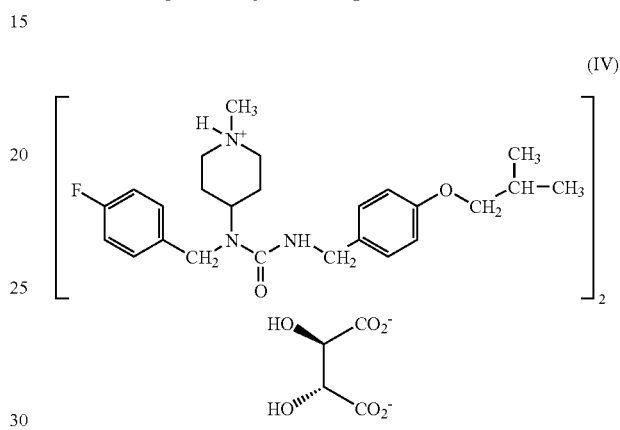

(IV)

Another embodiment disclosed herein includes a method of inhibiting an activity of a monoamine receptor, comprising administering to a subject a compound of formula IV:

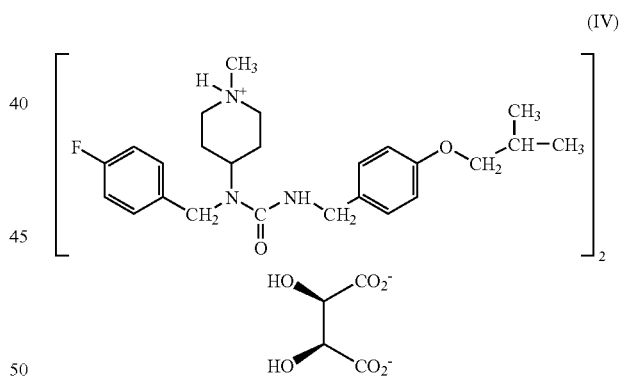

(IV)

Another embodiment disclosed herein includes a method for the treatment of neuropsychiatric diseases, comprising administering to a subject a compound of formula IV:

(IV)

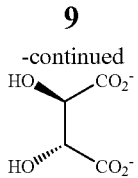

In some embodiments, the neuropsychiatric disease is selected from the group consisting of psychosis, schizophrenia, schizoaffective disorders, mania, psychotic depression, affective disorders, dementia, anxiety, sleep disorders, appetite disorders, bipolar disorder, psychosis secondary to hypertension, migraine, vasospasm, and ischemia, motor tics, tremor, psychomotor slowing, bradykinesia, and neuropathic pain.

Another embodiment disclosed herein includes a method for the treatment of neurodegenerative diseases, comprising administering to a subject the compound of formula IV. In some embodiments, the neurodegenerative disease is selected from the group consisting Parkinson's disease, Huntington's disease, Alzheimer's disease, Spinocerebellar Atrophy, Tourette's Syndrome, Friedrich's Ataxia, Machado-Joseph's disease, Lewy Body Dementia, Dystonia, Progressive Supranuclear Palsy, and Frontotemporal Dementia.

Another embodiment disclosed herein includes a method for treating dyskinesia associated with dopaminergic therapy, comprising administering to a subject the compound of formula IV.

Another embodiment disclosed herein includes a method for treating dystonia, myoclonus, or tremor associated with dopaminergic therapy, comprising administering to a subject the compound of formula IV.

Another embodiment disclosed herein includes a method for treating a thrombotic condition, comprising administering to a subject the compound of formula IV. In some embodiments, the thrombotic condition is selected from the group consisting of myocardial infarction, thrombotic or ischemic stroke, idiopathic and thrombotic thrombocytopenic purpura, peripheral vascular disease, and Raynaud's disease.

DETAILED DESCRIPTION OF THE PREFERRED EMBODIMENT

Figure 1:
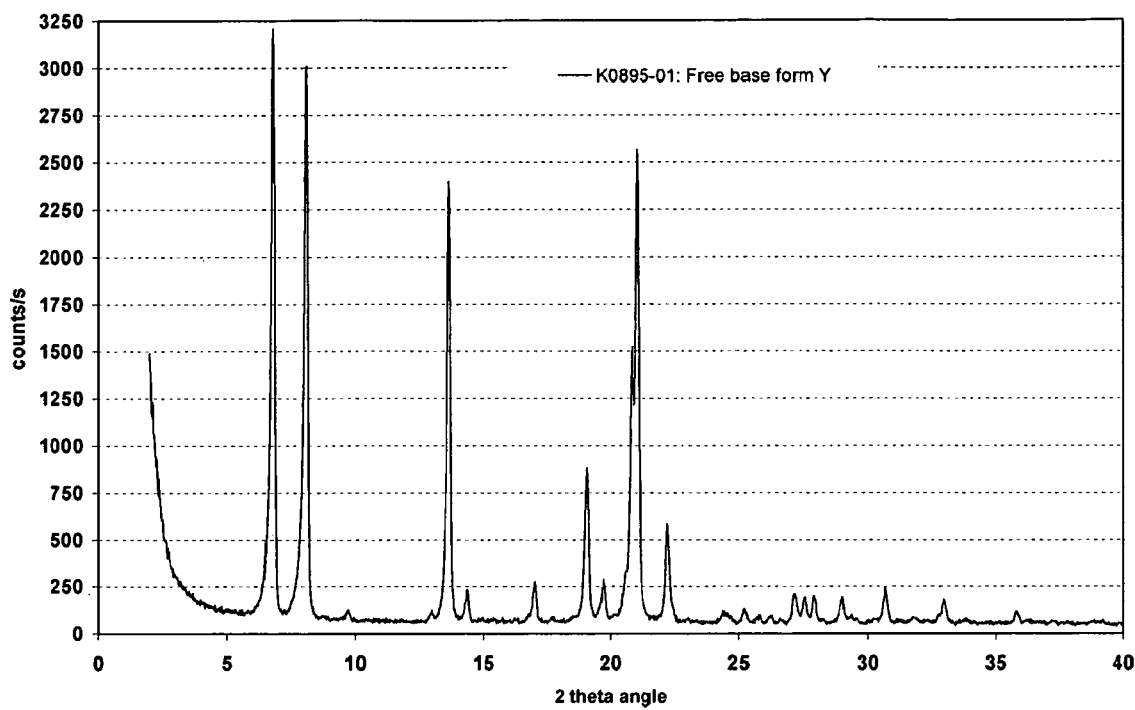
FIG. 1 is a X-ray powder diffraction pattern of crystal form Y of the free base compound of formula I.

One useful N-azacycloalkyl-N-aralkyl carbamide is N-(4-fluorobenzyl)-N-(1-methylpiperidin-4-yl)-N'-(4-(2-methylpropyloxy)phenylmethyl)carbamide of formula I:

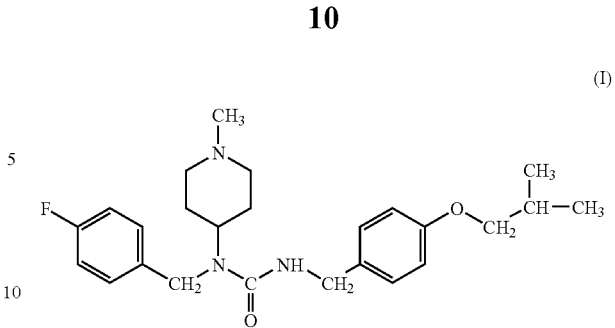

Synthesis of N-(4-fluorobenzyl)-N-(1-methylpiperidin-4-yl)-N'-(4-(2-methylpropyloxy)phenylmethyl) carbamide One embodiment is a method of synthesizing the compound of formula (I) comprising reacting the compound of formula II ((4-fluorobenzyl)-(1-methylpiperidin-4-yl)amine)

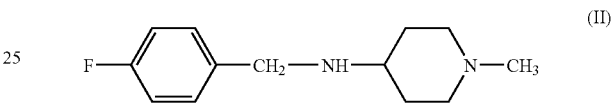

with the compound of formula III (4-(2-methylpropyloxy) phenylmethyl-isocyanate)

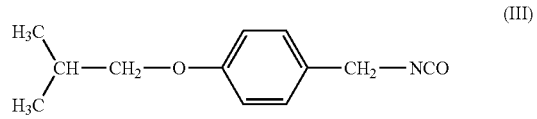

In one embodiment, about 0.9 to about 1.1 equivalents of (4-fluorobenzyl)-(1-methylpiperidin-4-yl)amine per equivalent of 4-(2-methylpropyloxy)phenylmethyl-isocyanate is used. In some embodiments, the resulting compound of formula I is isolated from the reaction mixture. In one embodiment, a salt-forming acid is added after the reaction. The formed salt may be isolated by solvent removal, precipitation, or both solvent removal and precipitation, followed by deliberation of the compound of formula I under alkaline aqueous conditions through dissolution in an organic solvent in a two phase system, and separating the compound of formula I from the organic solution. In a preferred embodiment, 1.0 equivalent of (4-fluorobenzyl)-(1-methylpiperidin-4-yl)amine per equivalent of 4-(2-methylpropyloxy)phenylmethyl-isocyanate is used in the reaction. The reaction may be carried out in the presence of Lewis acids as catalysts such as metal salts or more preferably metal alkoxylates. Some examples are $MgCl_2$, $FeCl_2$, $FeCl_3$, $FeBr_2$, $Fe(SO_4)_2$, $NiCl_2$, $BCl_3$, $AlCl_3$, $BBr_3$, $TiCl_4$, $TiBr_4$, $ZrCl_4$, $BCl_3$, $Al(O-C_1-C_4-Alkyl)_3$, and $Ti(O-C_1-C_4-Alkyl)_3$. The amount of catalyst may be from about 0.0001 to about 5 percent by weight and preferably about 0.01 to about 3 percent by weight relative to the compound of formula II.

The reaction is preferably carried out in the presence of an inert organic solvent such as aliphatic ethers (e.g., diethyl ether, methyl propyl ether, dibutyl ether, ethylene glycol dimethyl ether, tetrahydrofuran or dioxane), esters of aliphatic carboxylic acids or alcohols (e.g., $C_2$-$C_4$ alkyl esters of acetic acid), lactones (e.g., valerolactone), halogenated hydrocarbons (e.g., di- or trichloromethane, tetrachloroethane), or aliphatic $C_3$-$C_8$ ketones (e.g., acetone, methyl propyl ketone, diethyl ketone, or methyl i- or t-butyl ketone).

The reaction temperature is preferably in the range of about −30° C. to about 60° C. and more preferably in the range of about 5° C. to about 30° C. The reaction time may be controlled by monitoring the consumption of the compound of formula II or formula III either by on-line process analytics, or by recovering and analyzing samples offline.

Isolation of the compound of formula I may be performed by any suitable method including removal of the solvent by distillation of the reaction residue under reduced pressure and lower temperatures, such as up to about 100° C., preferably up to about 80° C. Isolation may also occur by partial removal of solvent to increase the concentration, filtering of impurities, precipitating the solid compound of formula I either by further concentration or addition of a non-solvent such as an aliphatic hydrocarbon (e.g., pentane, hexane, heptane, octane, cyclohexane, methylcyclohexane, or water), filtering of the solid, and drying. The isolated compound of formula I may be purified by known methods such as distillation or chromatographic methods.

It was found that removal of impurities such as formed side-products prior to the isolation is a convenient route to produce the compound of formula I with high purity. It was further found that purification can be effectively improved by forming salts of the carbamide, which can be precipitated as crystalline compounds and re-crystallized from solvents to remove impurities. The free carbamide of formula I is then deliberated by dissolution of the salt in water, addition of a base, and extraction of the carbamide with an organic solvent. The organic solutions may be washed with water and aqueous sodium chloride before removal of the solvent by distillation, optionally under reduced pressure. Impurities may be removed in this method by precipitation or dissolution in water in then use of a two phase systems. When precipitation of the salt is desired for easy isolation by filtration or centrifugation, partial removal of the organic solvent and addition of fresh solvent may be carried out. Suitable solvents with low salt solubility are aprotic organic solvents such as hydrocarbons, halogenated hydrocarbons, ethers, ketones, carboxylic acid esters and lactones, acetonitrile, and alcohols having at least 3 carbon atoms.

Salt forming acids may be selected from inorganic or organic acids, such as mineral acids (HCl, HBr, HI, $H_2SO_4$), mono- or dicarboxylic acids (formic acid, acetic acid, oxalic acid, malonic acid, maleic acid, fumaric acid, succinic acid, tartaric acid) or sulfonic acids (methylsulfonic acid). The acids may be added as aqueous solutions in amounts sufficient to form a solid or crystalline precipitate. The amount may range from about 0.5 to about 2 equivalents relative to the compound of formula I, depending mainly on the functionality of the acid and the desired excess for complete and fast salt formation.

The salts may be dissolved in water and a non-water miscible organic solvent for the compound of formula I added to dissolve the deliberated compound of formula I when the base is added. Suitable bases include, but are not limited to, alkaline earth metal hydroxides such as LiOH, NaOH or KOH. In one embodiment, the pH of the aqueous phase is greater than about 8.5. The reaction may be terminated from minutes to 1 hour. The reaction is preferably stopped after 5 to 30 minutes. The organic phase is then separated, optionally washed with water and brine and/or filtered. The desired product may be obtained by removal of the solvent and drying, or by precipitation with a non-solvent, filtration, and drying of the solid residue. The compound of formula I is obtained in high purity and yields.

The starting materials for the above-described reaction can be obtained by known and analogous methods. Specifically, the compound of formula II may be obtained by the reaction of N-methylpiperidine-4-one with 4-fluorobenzylamine in the presence of a metal hydride, for example according to the scheme

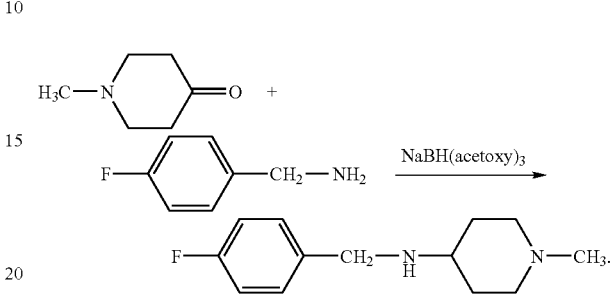

Compounds of formula III may be prepared by reacting 4-hydroxybenzaldehyde with isobutylhalogenide (e.g., isobutylbromide) to form 4-isobutoxybenzaldehyde, which may be converted with hydroxylamine to the aldoxime form:

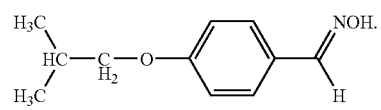

This oxime may be catalytically hydrogenated with a palladium catalyst to the corresponding 4-isobutoxybenzylamine, from which the isocyanate of formula III may be obtained by reaction with phosgene.

Crystalline form of N-(4-fluorobenzyl)-N-(1-methylpiperidin-4-yl)-N'-(4-(2-methylpropyloxy)phenylmethyl)carbamide (Form Y)

Using the above-described method, the compound of formula I is generally obtained as a substantially amorphous solid, which may be admixed with small amounts of a crystalline form. It was surprisingly found that a pure crystalline form can be obtained from the salt form, such as the hemitartrate salt, when deliberating the base under certain condition. This crystallisation can even be used to purify the base by re-crystallization of salts or by re-crystallization of the base itself.

Accordingly, in one embodiment, a crystalline form of N-(4-fluorobenzyl)-N-(1-methylpiperidin-4-yl)-N'-(4-(2-methylpropyloxy)phenylmethyl)carbamide is provided that exhibits a characteristic melting point of about 124° C. (peak temperature), determined with Differential Scanning Calometry (DSC) at a heating rate of 10° C./minute, hereinafter designated as form Y. The enthalpy of fusion of form Y is about 99 J/g.

The X-ray powder diffraction pattern of form Y is depicted in FIG. 1. Specifically the X-ray powder diffraction pattern exhibits the following characteristic peaks expressed in d-values (Å): 13.0 (vs), 10.9 (vs), 6.8 (vw), 6.5 (s), 6.2 (w), 5.2 (w), 4.7 (m), 4.5 (w), 4.3 (s), 4.22 (vs), 4.00 (m), 3.53 (vw), 3.40 (vw), 3.28 (w), 3.24 (w), 3.19 (w), 3.08 (w), 2.91 (w), and 2.72 (w). The abbreviations in parenthesis are used herein as follows: (vs)=very strong intensity, (s)=strong intensity, (m)=medium intensity, (w)=weak intensity, and (vw)=very weak intensity. In various embodiments, form Y is present in a solid form of the compound of formula I in amounts of at least about 50%, 70%, 80%, 90%, 95%, or 98%, with the remainder being other crystalline forms (including hydrates and solvates) and/or amorphous forms.

Form Y is a very thermodynamically stable form of the compound of formula I. Powder X-ray diffraction and DSC indicate the crystalline character of form Y, and analysis of the elemental composition complies with compound of formula I. The crystalline form Y of formula I is obtained as a white powder.

The compound of formula I is soluble in various organic solvents and shows a low solubility in water. In contrast, salts of the compound of formula I are well soluble in water. These properties can be used for the preparation of Form Y of the compound of formula I. For example, one process for forming Form Y includes:

a) dissolution in water under stirring of a salt form of formula I, preferably the hemitartrate salt;
b) addition of a sufficient amount of an organic aprotic solvent for the dissolution of the formed compound of formula. I;
c) adjusting of the pH of the aqueous salt solution to a value of at least 8.5 by addition of a base;
d) optionally extracting the aqueous phase with the organic solvent and collecting all organic phases;
e) removing a part of the solvent and cooling the remaining organic solution to less than 15° C.;
f) holding at this temperature while optionally stirring; and
g) filtering off the precipitate, washing the solid residue, and drying it.

The mother liquor can be again concentrated and cooled to increase the yield. Salt forming acids may be selected from inorganic or organic acids, such as mineral acids (e.g., HCl, HBr, HI, $H_2SO_4$, $H_3PO_4$), mono- or dicarboxylic acids (e.g., formic acid, acetic acid, oxalic acid, malonic acid, tartaric acid, maleic acid, fumaric acid, succinic acid), sulfonic acids (e.g., methylsulfonic acid), citric acid, glucuronic acid, malic acid, pamoic acid, or ethane-1,2-disulfonic acid.

Suitable solvents are hydrocarbons such as toluene, halogenated hydrocarbons such as di- or trichloromethane, tetrachloroethane, esters of aliphatic carboxylic acids and alcohols ($C_2$-$C_4$alkyl esters of acetic acid) (ethyl acetate), lactones (valerolactone), ethers (diethylether, methylpropyl ether, t-butyl-methyl-ether, dibutyl ether, dimethyl ether), aliphatic $C_4$-$C_5$ketones (methyl propyl ketone, diethyl ketone or methyl i- or t-butyl ketone). The pH value in step c) may be advantageously adjusted to at least 9.5. Suitable bases include, but are not limited to aqueous alkaline or earth alkaline metal hydroxides such as LiOH, NaOH, KOH or Ca(OH)$_2$.

Removal of a part of the solvent mainly serves to concentrate the organic solution so that it contains about 5 to about 30 percent by weight of the compound of formula I. The cooling temperature is preferably in the range of about −10 to about 10° C. and most preferably about 0° C. to about 10° C. Storage time at this temperature optionally under stirring is preferably about 30 minutes to about 12 hours. Removal of residual solvent may be carried out in a conventional manner under vacuum, in an inert gas flow, or both.

Formation of N-(4-fluorobenzyl)-N-(1-methylpiperidin-4-yl)-N'-(4-(2-methylpropyloxy)phenylmethyl) carbamide hemi-tartrate The compound of formula I has a low solubility in water. Accordingly, in some embodiments, forms of the compound are provided that are water soluble and hence have enhanced bioavailability and improved processing characteristics for the preparation and formulation of drug compositions. It was found that a hemi-tartrate of N-(4-fluorobenzyl)-N-(1-methylpiperidin-4-yl)-N'-(4-(2-methylpropyloxy)phenylmethyl) carbamide is particularly suitable. Accordingly, one embodiment provides N-(4-fluorobenzyl)-N-(1-methylpiperidin-4-yl)-N'-(4-(2-methylpropyloxy)phenylmethyl)carbamide hemi-tartrate according to the formula IV,

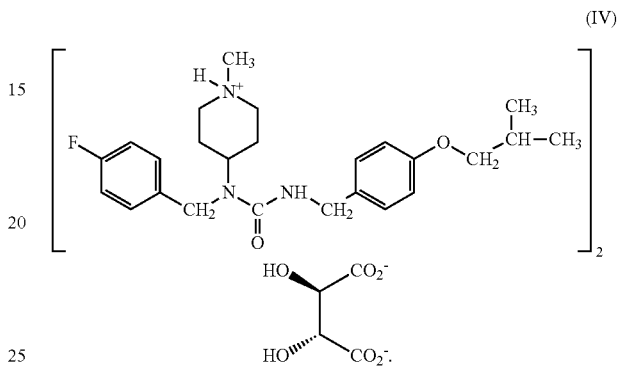

The compound of formula IV may be prepared as an integrated part of the process for synthesizing the compound of formula I as described above by using tartaric acid as the salt forming acid. Alternatively, the tartrate salt may be formed by reaction of the isolated compound of formula I with tartaric acid.

In one embodiment, N-(4-fluorobenzyl)-N-(1-methylpiperidin-4-yl)-N'-(4-(2-methylpropyloxy)phenylmethyl)carbamide hemi-tartrate is formed according to the following method:

a) react about 0.9 to about 1.1 equivalents of (4-fluorobenzyl)-(1-methylpiperidin-4-yl)amine of formula II

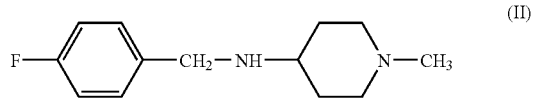

with 1 equivalent of 4-(2-methylpropyloxy)phenylmethylisocyanate of formula III

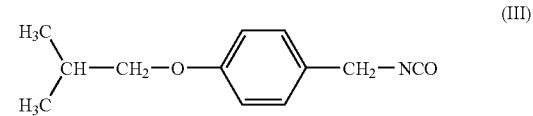

b) add tartaric acid, and
c) isolate the hemi-tartrate of the compound of formula I from the obtained suspension.

The hemi-tartrate may also be obtained through precipitation by cooling, solvent removal, adding a non-solvent, or a combination of these methods. In one embodiment, one or more solvents are added in step b) that have a low solubility for the hemi-tartrate, such as isopropyl acetate, a ketone (such as acetone or 2-butanone), and/or tetrahydrofuran. The temperature in step b) is preferably from about 15 to about 30° C. The hemi-tartrate precipitates and forms a suspension, which may be stirred for up to 3 days before filtering off the solid from the reaction mixture preferably at ambient conditions. The solid residue may be washed, and then dried at temperatures up to 50° C., if desired, under vacuum.

The hemi-tartrate of formula IV is obtained in high yields and purity. The mother liquors can be used to isolate more hemi-tartrate of formula IV in the usual manner. The hemi-tartrate may be further purified by conversion to the free base of formula I and isolating a solution of the base, which is then used to re-precipitate the hemi-tartrate by the addition of tartaric acid.

Crystalline forms of N-(4-fluorobenzyl)-N-(1-methylpiperidin-4-yl)-N'-(4-(2-methylpropyloxy)phenylmethyl)carbamide hemi-tartrate (Forms A-C)

It was surprisingly found that the compound of formula IV can be obtained in a number of crystalline forms. One such crystalline solid form produced by the above-described method is hereinafter referred to crystalline form A. Crystalline form A generally contains some water as demonstrated when subjected to heat in thermogravimetric analysis coupled to FT infrared spectroscopy, or by Karl Fischer titration. The water content may range up to an amount of about 2 to 3 percent by weight, which would generally correspond to a hemi-hydrate. However, the water is only weakly bound, since the weight loss starts just above ambient temperature and is complete at about 150° C. The water can also easily be removed by treatment with dry nitrogen for a longer time (about up to 20 hours) and form A can also exist in a water-free state. DSC indicates that the melting point of the dehydrated form A is about 133-135° C. (peak temperature) with an enthalpy of fusion of about 70 J/g. Form A shows a considerable water uptake when exposed to humidity, especially above 75% relative humidity. The water is given off when the relative humidity is decreased to 50% and less. This behaviour is typical for a deliquescent solid. The compound of formula IV as crystalline form A is well soluble in methanol, water, or organic solvents admixed with water. The compound of formula IV shows a low solubility in other organic solvents. Crystalline form A may contain smaller amounts of crystalline form C (described below), when manufactured according to the above process.

Figure 2:
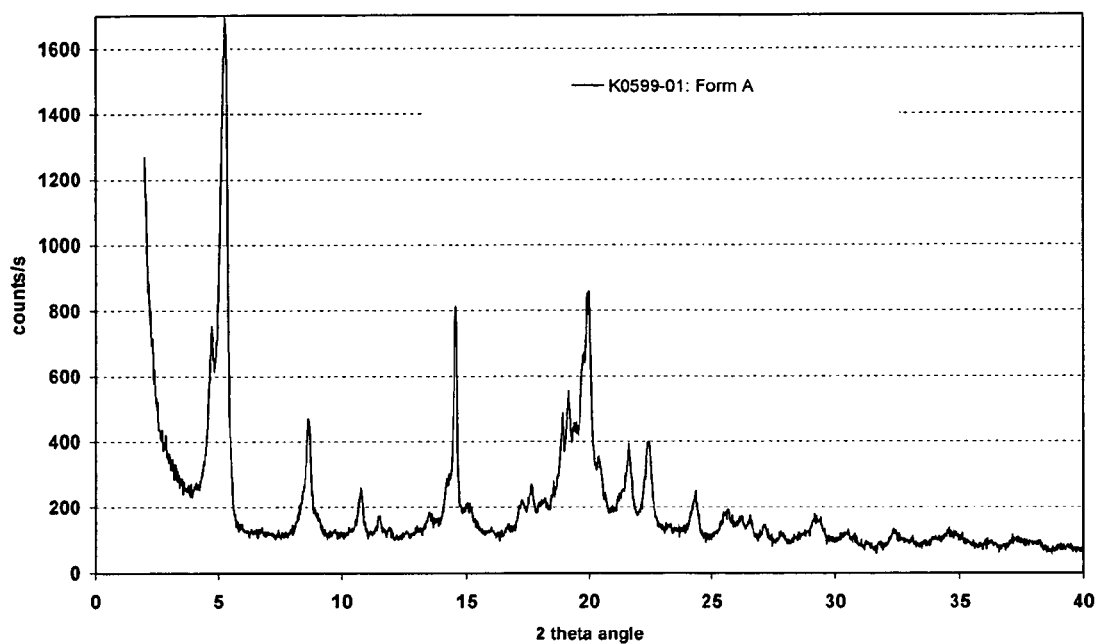
FIG. 2 is a X-ray powder diffraction pattern of crystal form A of the compound of formula IV.

The X-ray powder diffraction pattern of form A is depicted in FIG. 2. Specifically the X-ray powder diffraction pattern exhibits the following characteristic peaks expressed in d-values (Å): 18.6 (s), 16.7 (vs), 10.2 (s), 8.2 (m), 7.7 (w), 7.4 (w), 6.5 (w), 6.2 (m), 6.1 (vs), 5.86 (w), 5.14 (m), 5.03 (m), 4.78 (m), 4.69 (m), 4.63 (s), 4.49 (s), 4.44 (vs), 4.35 (m), 4.10 (m), 3.96 (s), and 3.66 (m). In various embodiments, form A is present in a solid form of the compound of formula IV in amounts of at least about 50%, 70%, 80%, 90%, 95%, or 98%, with the remainder being other crystalline forms (including hydrates and solvates) and/or amorphous forms.

Crystalline form A can be prepared in a controlled manner by crystallization from ethanol, optionally admixed with isopropanol. Accordingly, one embodiment is a process for the preparation of crystalline form A that includes:
  a) dissolving the compound of formula IV in ethanol or an admixture of ethanol and isopropanol at elevated temperature;
  b) slowly cooling the solution to a temperature of less than 20° C.; and
  c) filtering off the precipitated solid and drying it.

In some embodiments, the mixtures of ethanol and isopropanol may contain up to about 15 and more preferably up to 10 volume percent isopropanol. Ethanol is the preferred solvent. It is also preferred to use dried ethanol, optionally in admixture with dry isopropanol. In some embodiments, the elevated temperature is from about 55 to about 90° C. and preferably from about 55 to about 65° C. The mixture is stirred at elevated temperatures until the compound of formula IV is completely dissolved. Slow cooling may mean a cooling rate of about 0.1 to about 3° C./minute, preferably about 0.2 to about 2° C./minute, and particularly about 0.2 to about 1° C./minute. Crystallization started at below about 50° C. and it was observed that a thick paste can form when stirring at such a temperature for about 1 hour. Heating again to the higher temperature and then cooling again generally results in a suspension, which can be stirred at about 40 to about 50° C. and also when further cooling to a temperature of less than about 20° C., preferably about 5 to about 15° C. The cooling rate after stirring may be about 0.1 to about 3° C./minute and preferably about 0.3 to about 1° C./minute. The resulting crystalline solid is then filtered off and dried by sucking dry air through the filter cake at temperatures of about 25 to less than about 40° C., preferably at about 30° C. Drying may be completed by keeping the pre-dried solid for a certain time under vacuum at ambient or elevated temperature.

The compound of formula IV can be transformed to a completely amorphous form by dissolving the compound in a solvent such as for example water and lyophilizing the solution. The amorphous form can then be used to manufacture other polymorphic or pseudo-polymorphic forms.

In one embodiment, another crystalline form of the compound of formula IV is prepared using phase equilibration processes in a reproducible manner using ethyl acetate, acetone, methyl-ethyl ketone, or acetonitrile as solvent. This crystalline solid is hereinafter referred to crystalline form B. Crystalline form B may contain some water, as demonstrated when subjected to heat in thermogravimetric analysis coupled to FT infrared spectroscopy, or by Karl Fischer titration. The water content may range up to an amount of about 3.4 percent by weight. This amount generally indicates a monohydrate stable under ambient conditions (theoretical content would be 3.5%). However, water is only weakly bound, since a weight loss is observed at ambient temperature and low relative humidity of about less than 20% and form B can also exist in a water-free state. The melting point of the dehydrated form B is about 135° C. with an enthalpy of fusion of about 71 J/g. Form B shows a considerable water uptake when exposed to high humidity, especially above 80% relative humidity. However, the hygroscopicity is less pronounced than observed in form A and no deliquescence is found at high relative humidity of about 90%.

Figure 3:
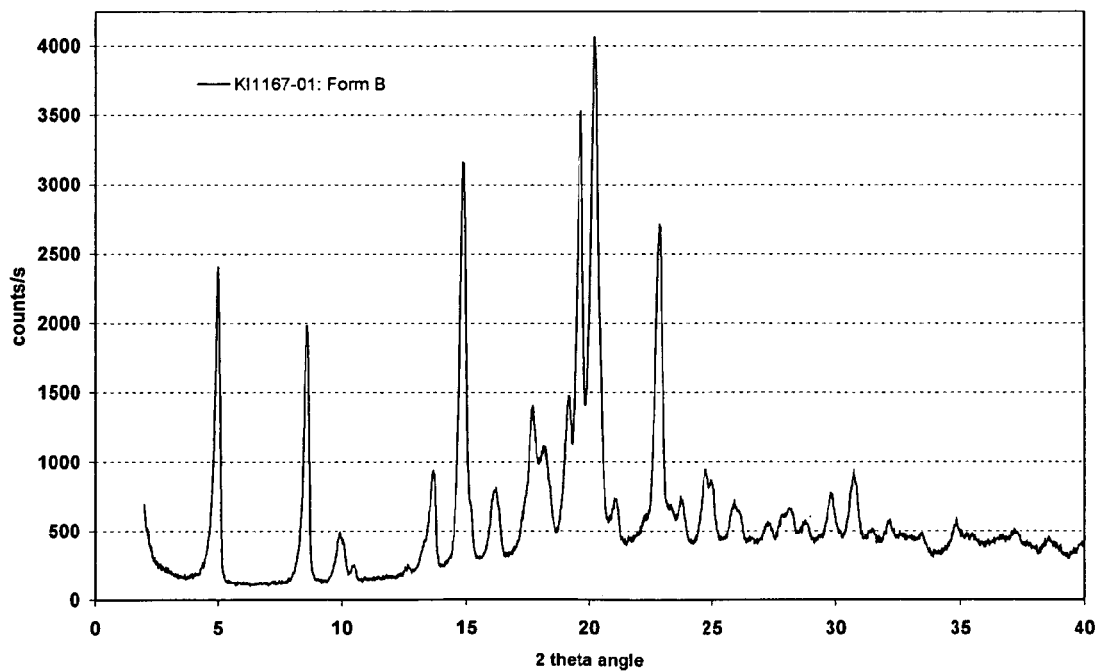
FIG. 3 is a X-ray powder diffraction pattern of crystal form B of the compound of formula IV.

The X-ray powder diffraction pattern of form B is depicted in FIG. 3. Specifically the X-ray powder diffraction pattern exhibits the following characteristic peaks expressed in d-values (Å): 7.4 (vs), 10.2 (s), 8.8 (w), 6.4 (w), 5.91 (vs), 5.46 (w), 4.99 (m), 4.90 (m), 4.62 (m), 4.50 (vs), 4.37 (vs), 4.20 (w), 3.87 (vs), 3.73 (w), 3.58 (m), 3.42 (w), and 2.90 (w). In various embodiments, form B is present in a solid form of the compound of formula IV in amounts of at least about 50%, 70%, 80%, 90%, 95%, or 98%, with the remainder being other crystalline forms (including hydrates and solvates) and/or amorphous forms.

Crystalline form B can be prepared in a controlled manner by various processes. In one embodiment, it is precipitated from solutions in polar solvents such as water or methylene chloride using non-solvents such as methylethylketone, heptane, toluene, acetonitrile or ethyl acetate at temperatures of 0-40° C., and subsequent phase equilibration substantially at room temperature. Another method is the equilibration of suspensions of other crystalline forms such as crystalline forms A or C or mixtures thereof in solvents such as acetonitrile, ethyl acetate, ethanol/methylethylketone, ethanol/acetone, ethyl acetate saturated with water, acetonitrile or ethyl acetate containing about 1 volume percent of water at a temperature from room temperature to about 40° C., optionally with temperature cycles. The equilibration of suspensions with the amorphous material of the compound of formula I at temperatures of 0 to about 45° C., optionally under the application of temperature cycles, is a further method for the preparation of form B. Suitable solvents are heptane, ethyl acetate, acetonitrile, methylethylketone, ethylacetate or tertiary-butylmethylether saturated with water, or ethyl acetate/ethanol containing 1 volume percent water.

It was observed that crystal form A from the hemi-tartrate production can contain to some extent another polymorph form and further investigation revealed that this polymorph is neither a hydrate nor a solvate. This crystalline solid is hereinafter referred to as crystalline form C. Crystalline form C may be prepared by suspension equilibration of crystalline forms A or B, preferably with addition of seeding crystals of form C. Crystalline form C is more thermodynamically and chemically stable than forms A or B. Crystalline form C absorbs much less water than form A. Water absorption at about 95% relative humidity is only about 1% and no deliquescence or hygroscopicity is observed. The exposure to humidity does not result in a change of the crystalline form. Crystalline form C is stable at 75% relative humidity in an open container and does not absorb water up to about 60° C. Thermogravimetric analysis results in a weight loss of about 0.9% below 150° C., which can be attributed to absorbed water. The investigation with DSC at a heating rate of 20° C. shows an endothermic signal at 177° C. with an enthalpy of fusion of about 129 J/g. The signal is attributed to the melting (peak) temperature, whereby first decomposition of the substance is observed above 170° C. Solubility of crystalline form C in water is very high. Crystalline form C is highly suitable as an active compound in the manufacturing and formulation of drugs.

Figure 4:
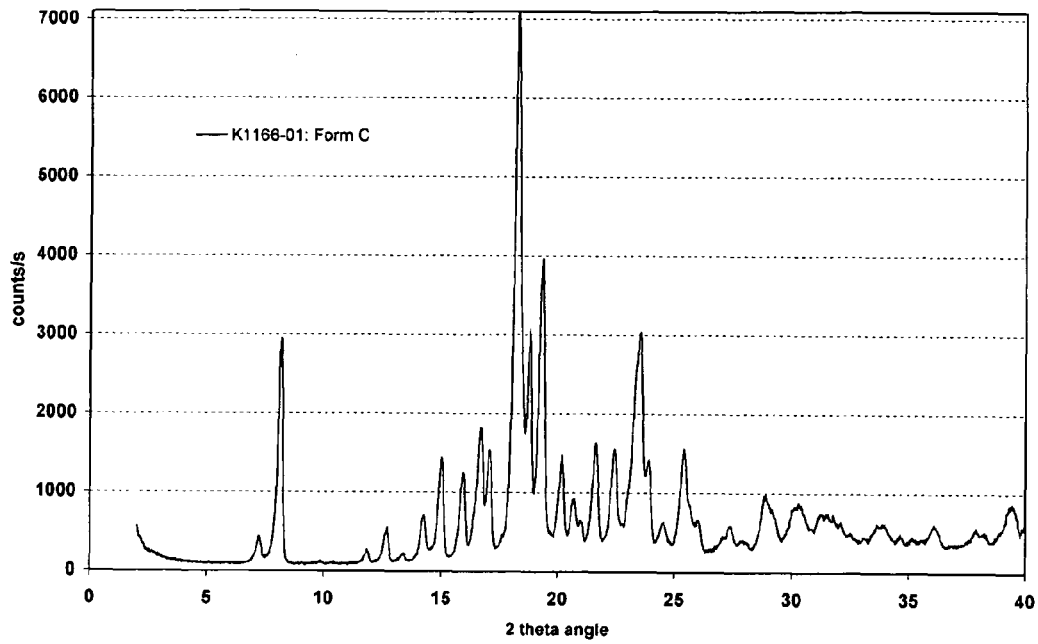
FIG. 4 is a X-ray powder diffraction pattern of crystal form C of the compound of formula IV.

The X-ray powder diffraction pattern of form C is depicted in FIG. 4. Specifically the X-ray powder diffraction pattern exhibits the following characteristic peaks expressed in d-values (Å): 12.0 (w), 10.7 (vs), 7.4 (vw), 6.9 (vw), 6.6 (vw), 6.2 (w), 5.86 (m), 5.53 (w), 5.28 (m), 5.16 (m), 4.84 (vs), 4.70 (m), 4.57 (s), 4.38 (m), 4.09 (w), 3.94 (w), 3.77 (s), 3.71 (m), 3.49 (w), 3.46 (w), 3.25 (w), 3.08 (w), and 2.93 (w). In various embodiments, form C is present in a solid form of the compound of formula IV in amounts of at least about 50%, 70%, 80%, 90%, 95%, or 98%, with the remainder being other crystalline forms (including hydrates and solvates) and/or amorphous forms.

In one embodiment, a process is provided for the preparation of pure crystalline form C on a large scale for industrial production of the pharmaceutically active compound. It was found that the crystallization from heated and then cooled solutions does not readily result in form C. It was further found that form C can be manufactured in a controlled manner, when crystalline forms A or B are equilibrated in suspension in the presence of a polar and aprotic solvent and seed crystals of form C are added. In an alternative to using seed crystals, a starting material may be used that contains some crystal form C after preparation of the compound of formula IV. The solid in the suspension may have crystals with a particle size in the range of 1 to about 200 and preferably 2 to 100 μm, which can be filtered off, washed and dried under moderate conditions; e.g., for instance at 60° C. under vacuum. The particle size obtained may be dependent on the manufacture scale, on the solvent or solvent mixture used, on the cooling rate, and the number of added seeding crystals.

One method for the preparation of crystalline form C comprises forming a suspension of a solid compound of formula IV in an aprotic solvent at elevated temperature and stirring the suspension, optionally adding crystal seeds of form C, until substantial complete conversion in pure form C.

The temperature of the process may be from 20 to 100° C. and preferably 40 to 80° C. Suitable solvents for conversion to form C may be selected from the group comprising aliphatic or cyclic ethers, carboxylic esters, lactones, alkanes and aliphatic $C_3$-$C_8$ ketones. Seeding with crystals of form C is preferably carried out when the solid form is in part dissolved and a saturated solution is formed in which the solid form is suspended. Seeding is carried out preferably in a temperature range from 40 to 80° C. and more preferably from 55 to 65° C. Stirring time of the suspension may be from 30 minutes to days, and most preferably from 30 minutes to 6 hours. The suspension is slowly cooled before isolation of the solid by filtration or centrifugation and the cooling rate may be from 0.1 to 1° C./minute. Cooling may be carried out to an end temperature near room temperature or below.

One embodiment is a process for the preparation of crystalline form C of N-(4-fluorobenzyl)-N-(1-methylpiperidin-4-yl)-N'-(4-(2-methylpropyloxy)phenylmethyl)-carbamide tartrate of formula IV, comprising:

a) suspending the amorphous form or crystalline forms A, B, D, E, or F or mixtures thereof under stirring in a polar and aprotic solvent at temperatures from 30 to 70° C.;

b) continuing stirring at temperatures from 30 to 70° C. and adding crystal seeds of crystalline form C, when crystalline form C is not present in the starting material;

c) continuing stirring at temperatures from 30 to 70° C. until formation of crystalline form C is completed;

d) cooling to the process end temperature;

e) isolating of the crystalline solid from the suspension; and f) optionally washing and then drying the crystalline solid.

Crystalline form A may be used as the starting material, but the process can also be carried out with forms B, D, E, and F, or with an amorphous form. The starting material may advantageously be dried prior to use. Drying at 40° C. under vacuum is generally sufficient to remove unwanted residual solvents (e.g., alcohols, water, or mixtures thereof) which are detrimental to the formation of form C. Suitable solvents for crystallization of form C may be selected from the group comprising ethers, carboxylic esters, lactones and aliphatic ketones. Some specific examples and preferred solvents are diethylether, propyl methyl ether, t-butyl methyl ether, tetrahydrofuran, ethyl acetate, t-butyl methyl ketone, acetone, and methyl ethyl ketone. Most preferred solvent are ketones and especially preferred is methyl ethyl ketone and tetrahydrofuran. The amounts of crystalline forms A or B in the suspension, when used as starting materials, are not critical and the amount is chosen such that the suspension can be stirred at the applied temperatures. The temperature in step a) is preferably at about room temperature.

The temperature in steps b) and c) may range from 10 to 60° C. It may be advantageous to apply temperature cycles between higher and lower temperatures. The amount of crystal seeds added may be from 0.01 to 10 and preferably 0.1 to 5 percent by weight, referred to the amount of crystalline forms A and/or B. The addition of crystal seeds is in general preferred in order to accelerate the transformation of the crystalline forms.

Stirring in step c) may be continued for hours to days, for example, 0.5 hours to 3 days and preferably 2 hours to about 2 days. The transformation/conversion time substantially depends on the scale, the temperature, the solvent used, agitating intensity, and the amount of crystal seeds added to the suspension. The conversion time may be controlled by monitoring the ratio of the disappearing form and the produced form C either by on-line process analytics, or by recovering and analyzing samples off-line.

Isolation of the crystalline solid can be carried out by centrifugation or filtration. The product may be washed for example with a solvent and then dried over dry inert gas which can be pulled through the filter cake optionally under vacuum or applying vacuum for a time sufficient to remove the solvents. Further drying, either under vacuum and/or at moderate temperatures up to about 80° C. can be applied. It can be noted that form C exhibits excellent properties in terms of filtration and drying and a solid material is obtained that is essentially free of residual solvent; i.e., with less than 1000 ppm, preferably less than 200 ppm.

It was surprisingly found that crystalline form C can also be prepared by crystallization from a solution of the compound of formula IV in a selected solvent and seeding with crystalline form C at elevated temperature. Accordingly, in one embodiment, a method of preparing crystalline form C is provided, comprising:
 a) dissolving the amorphous form or crystalline forms A, B, D, E or F or mixtures thereof under stirring in a suitable solvent at temperatures from 0 to 70° C.;
 b) continuing stirring and adding crystal seeds of crystalline form C to the solution at elevated temperature; preferably at about 50 to 70° C. and most preferably at 55 to 65° C.;
 c) continuing agitation of the forming suspension at the same temperature for a time sufficient to convert the compound of formula IV in crystalline form C;
 d) cooling the obtained suspension at a cooling rate of 5 to 15° C. per hour to −20° C. to room temperature and preferably to 0 to 25° C.;
 e) isolating the crystalline solid from the suspension; and
 f) optionally washing and then drying the crystalline solid.

The amount of the compound of formula IV in step a) is chosen such that concentrated solutions are obtained. The concentration that can be reached depends on the solvent or solvent mixture used, and the solubility of the starting material. Tetrahydrofuran, and mixtures containing tetrahydrofuran are preferred as solvents since typically about 200 mg/ml of form A can be dissolved at reflux temperature. However, any solvent suitable at dissolving the starting material may be used. Non-limiting examples include tetrahydrofuran, acetone, ethanol, isopropanol, dichloromethane, 1,4-dioxane, and acetonitrile. The temperature in step a) is preferably from 40 to 70° C. The amount of added crystal seeds in step b) may be from 0.1 to 15% by weight and preferably from 2 to 10% by weight, referred to the amount of dissolved compound of formula IV. The agitation time in step c) depends on the scale and may range from about 20 minutes to about 24 hours, more preferably from 25 minutes to 12 hours, and most preferably from 30 minutes to 6 hours. The cooling rate in step d) is preferably from 8 to 12° C. per hour. Stirring may be continued after cooling at the cooling temperature range for up to 24, preferably 18 hours and more preferably 14 hours.

Crystalline form C can be obtained in high polymorphic purity. The material obtained with the processes described above may contain residual starting material, for example in amounts of up to 20 or up to 10 percent by weight relative to crystalline form C. These mixtures are also very suitable for drug formulations.

Solvates of N-(4-fluorobenzyl)-N-(1-methylpiperidin-4-yl)-N'-(4-(2-methylpropyloxy)phenylmethyl) carbamide hemi-tartrate (Forms D-F)

In some embodiments, the compound of formula IV may form various solvates with certain solvents. These pseudopolymorphic forms may be used in drug formulations or for the production of other polymorphic forms. In some embodiments, these solvates can exist either as solvated forms; i.e., containing a significant amount of the respective solvent, or in a corresponding non-solvated from; i.e., in a solvent-free form, wherein the crystalline structure is essentially retained.

One such solvate is formed by suspension equilibration of crystalline form A or an amorphous form of the compound of formula IV in isopropanol. After drying under nitrogen for about 30 minutes, the formed solvate contains about 6.0 to 6.6 percent by weight of isopropanol. The theoretical value for the hemi-isopropanolate is 5.6% content of isopropanol and it is concluded that the hemi-solvate has formed. The hemi-solvate with isopropanol is stable when exposed to 53% relative humidity in an open container. This form is herein referred to as crystalline form D.

Figure 5:
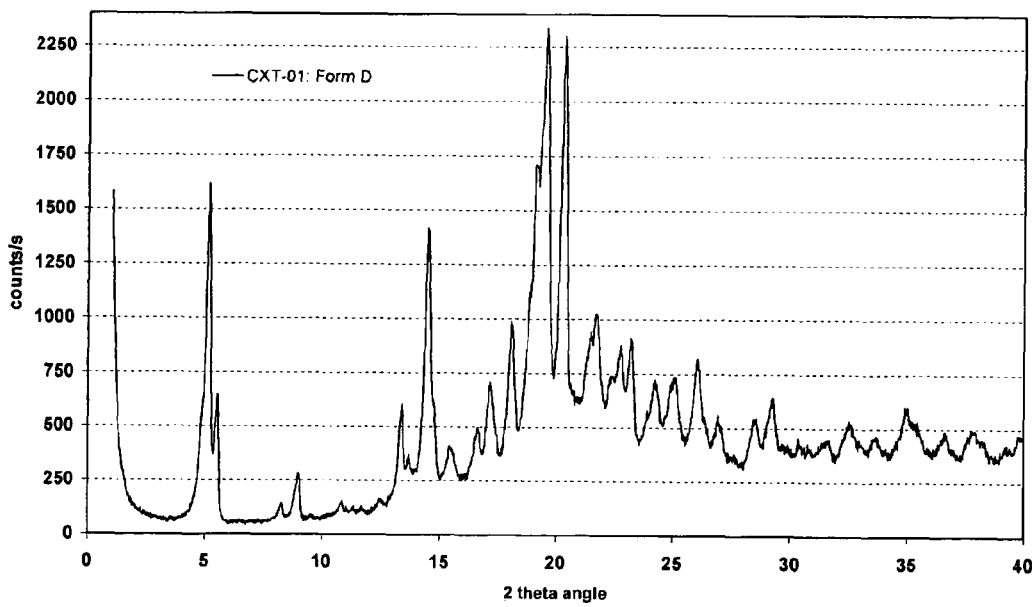
FIG. 5 is a X-ray powder diffraction pattern of crystal form D of the compound of formula IV.

The X-ray powder diffraction pattern of form D is depicted in FIG. 5. Specifically the X-ray powder diffraction pattern exhibits the following characteristic peaks expressed in d-values (Å): 17.2 (s), 16.0 (m), 10.7 (vw), 9.8 (w), 6.6 (m), 6.1 (s), 6.00 (m), 5.73 (w), 5.33 (w), 5.17 (m), 4.91 (m), 4.64 (s), 4.54 (vs), 4.37 (vs), 4.10 (m), 3.91 (m), 3.84 (m), 3.67, (w), 3.55 (m), 3.42 (m), 3.32 (w), 3.13 (w), and 3.06 (m). In various embodiments, form D is present in a solid form of the compound of formula IV in amounts of at least about 50%, 70%, 80%, 90%, 95%, or 98%, with the remainder being other crystalline forms (including hydrates and solvates) and/or amorphous forms.

It was further found that a t-butyl methyl ether (TBME) solvate may be formed, when the amorphous form of the compound of formula IV is subjected to phase equilibration in TBME at ambient temperature. The content of TBME is about 5% by weight relative to the compound of formula IV, measured by thermogravimetry at 10° C. heating rate. This form is herein referred to as crystalline form E.

Figure 6:
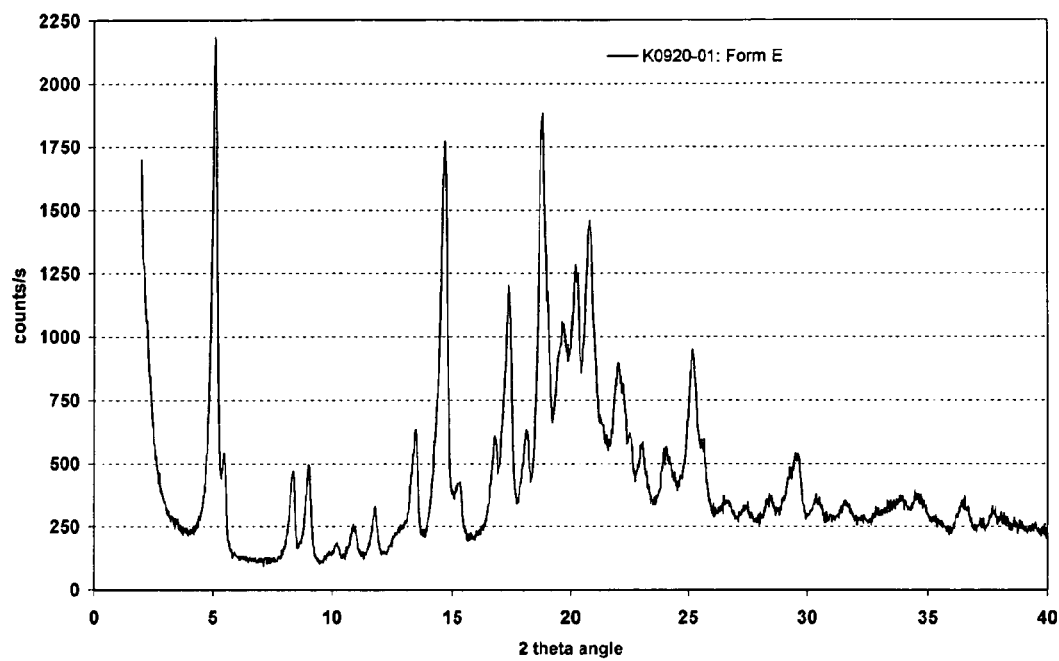
FIG. 6 is a X-ray powder diffraction pattern of crystal form E of the compound of formula IV.

The X-ray powder diffraction pattern of form E is depicted in FIG. 6. Specifically the X-ray powder diffraction pattern exhibits the following characteristic peaks expressed in d-values (Å): 17.3 (vs), 16.2 (m), 10.6 (m), 9.8 (m), 8.1 (w), 7.5 (w), 6.6 (m), 6.0 (vs), 5.28 (m), 5.09 (s), 4.90 (m), 4.72 (vs), 4.51 (m), 4.39 (s), 4.26 (s), 4.04 (m), 3.86 (w), 3.70 (w), 3.54 (m), 3.48 (m), 3.02 (w). In various embodiments, form E is present in a solid form of the compound of formula IV in amounts of at least about 50%, 70%, 80%, 90%, 95%, or 98%, with the remainder being other crystalline forms (including hydrates and solvates) and/or amorphous forms.

It was also found that the crystallisation of the compound of formula IV from a solution in tetrahydrofuran (THF) results in a non-stoichiometrical THF solvate, which contains from 0 to about 3% THF relative to the compound of formula IV, as measured by thermogravimetry at a heating rate of 10° C. The solvent release starts above ambient temperature and is complete near 130° C. This form is herein referred to as crystalline form F.

Figure 7:
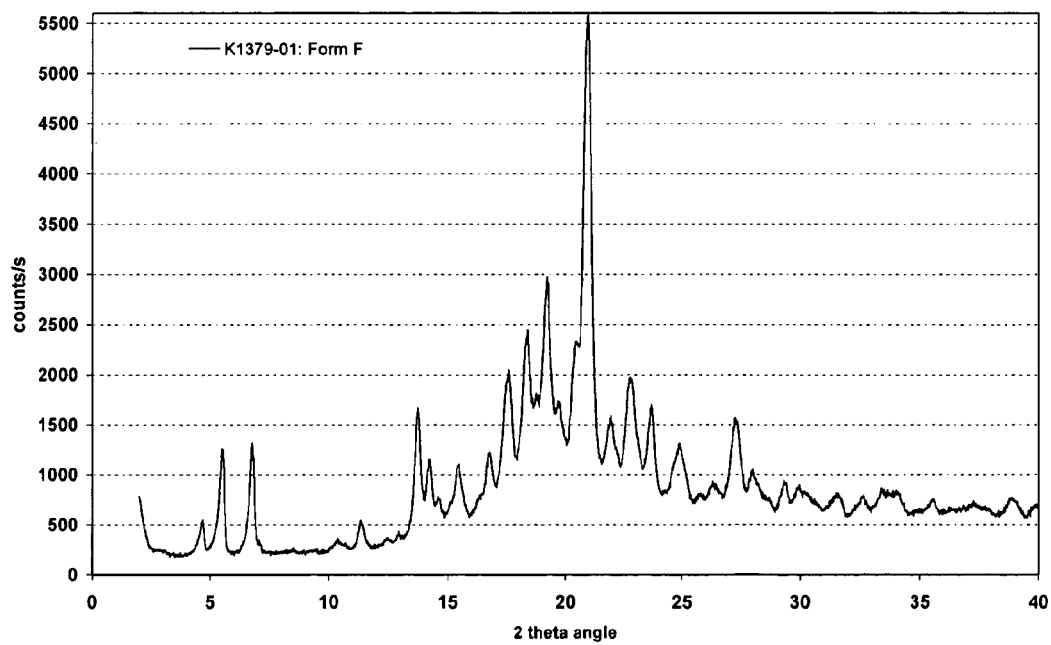
FIG. 7 is a X-ray powder diffraction pattern of crystal form F of the compound of formula IV.

The X-ray powder diffraction pattern of form F is depicted in FIG. 7. Specifically the X-ray powder diffraction pattern exhibits the following characteristic peaks expressed in d-values (Å): 19.0 (w), 16.0 (m), 13.0 (m), 7.8 (w), 6.4 (m), 6.2 (m), 5.74 (w), 5.29 (w), 5.04 (m), 4.83 (m), 4.62 (m), 4.50 (m), 4.34 (m), 4.24 (vs), 4.05 (m), 3.89 (m), 3.76 (m), 3.58 (w), and 3.27 (m). In various embodiments, form F is present in a solid form of the compound of formula IV in amounts of at least about 50%, 70%, 80%, 90%, 95%, or 98%, with the remainder being other crystalline forms (including hydrates and solvates) and/or amorphous forms.

Stability and Pharmaceutical Formulations

As mentioned above, the compound of formula IV is especially suitable as an active compound or pro-drug in pharmaceutical formulations to inhibit an activity of a monoamine receptor, preferably a serotonin receptor of the 5-HT2A subclass. The compound of formula IV has very good solubility in aqueous systems and the free base is deliberated at physiological pH ranges, providing a high bioavailability. The compound of formula IV also possesses high storage stability.

It was found that crystal form C is the most stable form of all found crystal forms. It was also found that crystal forms A and B are stable at ambient temperatures, stable in the presence of form C, and capable of coexisting with crystal form C. Crystal forms A, B and especially C are suitable for various types and a broad range of formulations, even in presence of humid components. These new crystal forms A, B and especially C present some advantages for manufacture, good handling due to convenient crystal size and morphology, very good stability under production conditions of various types of formulation, storage stability, high solubility, and high bioavailability. Crystal forms D, E and F may also be used for pharmaceutical formulations.

Form C is chemically very stable and can easily be formulated into tablets or any other pharmaceutically acceptable dosage form. Despite its high thermal stability it still exhibits favourable solubility properties as its aqueous solubility is greater than about 50 to 100 mg/ml. Forms A, B, D, E, and F exhibit high aqueous solubility of greater than 200 mg/ml. The solubility of all forms will depend on the pH in aqueous environments.

Forms A and B exhibit sufficient stability under ambient water partial pressures (i.e. at relative humidities between 20% and 75%). Furthermore, forms A and B are very suitable for pharmaceutical processing in aqueous environments; for instance, for granulation with water or with solvent-water mixtures.

Accordingly, some embodiments include pharmaceutical compositions comprising the compound of formula IV and a pharmaceutically acceptable carrier or diluent. In some embodiments, the compound of formula IV is selected from the group of crystalline forms A, B and C.

The amount of compound of formula IV required substantially depends on type of formulation and desired dosages during administration time periods. The amount in an oral formulation may be from 0.1 to 500 mg, preferably from 0.5 to 300 mg, and more preferably from 1 to 100 mg. Oral formulations may be solid formulations such as capsules, tablets, pills and troches, or liquid formulations such as aqueous suspensions, elixirs and syrups. Solid and liquid formulations encompass also incorporation of the compound of formula IV into liquid or solid food. Liquids also encompass solutions of the compound of formula IV for parenteral applications such as infusion or injection.

The crystal forms described above may be directly used as powder (e.g., micronized particles), granules, suspensions or solutions, or they may be combined together with other pharmaceutically acceptable ingredients in admixing the components and optionally finely divide them, and then filling capsules, composed for example from hard or soft gelatine, compressing tablets, pills or troches, or suspending or dissolving them in carriers for suspensions, elixirs and syrups. Coatings may be applied after compression to form pills.

Pharmaceutically acceptable ingredients are well known for the various types of formulations and may be for example binders such as natural or synthetic polymers, excipients, lubricants, surfactants, sweetening and flavouring agents, coating materials, preservatives, dyes, thickeners, adjuvants, antimicrobial agents, antioxidants and carriers for the various formulation types.

Examples for binders are gum tragacanth, acacia, starch, gelatine, and biological degradable polymers such as homo- or co-polyesters of dicarboxylic acids, alkylene glycols, polyalkylene glycols and/or aliphatic hydroxylcarboxylic acids; homo- or co-polyamides of dicarboxylic acids, alkylene diamines, and/or aliphatic amino carboxylic acids; corresponding polyester-polyamide-co-polymers, polyanhydrides, polyorthoesters, polyphosphazene and polycarbonates. The biological degradable polymers may be linear, branched or crosslinked. Specific examples are poly-glycolic acid, poly-lactic acid, and poly-d,l-lactide/glycolide. Other examples for polymers are water-soluble polymers such as polyoxaalkylenes (e.g., polyoxaethylene, polyoxapropylene and mixed polymers thereof), poly-acrylamides and hydroxyalkylated polyacrylamides, poly-maleic acid and esters or -amides thereof, poly-acrylic acid and esters or -amides thereof, poly-vinylalcohol and esters or -ethers thereof, poly-vinylimidazole, poly-vinylpyrrolidon, and natural polymers like chitosan.

Examples for excipients are phosphates such as dicalcium phosphate.

Examples for lubricants are natural or synthetic oils, fats, waxes, or fatty acid salts like magnesium stearate.

Surfactants may be anionic, cationic, amphoteric, or neutral. Examples for surfactants are lecithin, phospholipids, octyl sulfate, decyl sulfate, dodecyl sulfate, tetradecyl sulfate, hexadecyl sulfate and octadecyl sulfate, Na oleate or Na caprate, 1-acylaminoethane-2-sulfonic acids, such as 1-octanoylaminoethane-2-sulfonic acid, 1-decanoylaminoethane-2-sulfonic acid, 1-dodecanoylaminoethane-2-sulfonic acid, 1-tetradecanoylaminoethane-2-sulfonic acid, 1-hexadecanoylaminoethane-2-sulfonic acid, and 1-octadecanoylaminoethane-2-sulfonic acid, and taurocholic acid and taurodeoxycholic acid, bile acids and their salts, such as cholic acid, deoxycholic acid and sodium glycocholates, sodium caprate or sodium laurate, sodium oleate, sodium lauryl sulphate, sodium cetyl sulphate, sulfated castor oil and sodium dioctylsulfosuccinate, cocamidopropylbetaine and laurylbetaine, fatty alcohols, cholesterols, glycerol mono- or -distearate, glycerol mono- or -dioleate and glycerol mono- or -dipalmitate, and polyoxyethylene stearate.

Examples for sweetening agents are sucrose, fructose, lactose or aspartam.

Examples for flavouring agents are peppermint, oil of wintergreen or fruit flavours like cherry or orange flavour.

Examples for coating materials are gelatine, wax, shellac, sugar or biological degradable polymers.

Examples for preservatives are methyl or propylparabens, sorbic acid, chlorobutanol, phenol and thimerosal.

Examples for adjuvants are fragrances.

Examples for thickeners are synthetic polymers, fatty acids and fatty acid salts and esters and fatty alcohols.

Examples for antioxidants are vitamins, such as vitamin A, vitamin C, vitamin D or vitamin E, vegetable extracts or fish oils.

Examples for liquid carriers are water, alcohols such as ethanol, glycerol, propylene glycol, liquid polyethylene glycols, triacetin and oils. Examples for solid carriers are talc, clay, microcrystalline cellulose, silica, alumina and the like.

The pharmaceutical formulation according to the invention may also contain isotonic agents, such as sugars, buffers or sodium chloride.

The compound of formula IV according to the invention may also be formulated as effervescent tablet or powder, which disintegrates in an aqueous environment to provide a drinking solution.

A syrup or elixir may contain the compound of formula IV, sucrose or fructose as sweetening agent, a preservative like methylparaben, a dye, and a flavouring agent.

Slow release formulations may also be prepared from the compound of formula IV according to the invention in order to achieve a controlled release of the active agent in contact with the body fluids in the gastro intestinal tract, and to provide a substantial constant and effective level of the active agent in the blood plasma. The compound of formula IV may be embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

The compound of formula IV of this invention is also useful for administering a combination of therapeutic effective agents to an animal. Such a combination therapy can be carried out in using at least one further therapeutic agent which can be additionally dispersed or dissolved in a formulation. The compound of formula IV of this invention and its formulations respectively can be also administered in combination with other therapeutic agents that are effective to treat a given condition to provide a combination therapy.

The crystal form and the pharmaceutical compositions described herein are highly suitable for effective treatment of neuropsychiatric diseases including psychosis, affective disorders, dementia, neuropathic pain and hypertension.

One embodiment is a method of delivering the compound of formula I to a host, comprising administering to the host an effective amount of the compound of formula IV, such as crystalline forms A, B and C. A further embodiment is the use of the compound of formula IV for the manufacture of a medicament useful in the inhibition of an activity of a monoamine receptor, preferably a serotonin receptor of the 5-HT2A subclass.

One embodiment is a method for the treatment of neuropsychiatric diseases including the neuropsychiatric diseases selected from the group consisting of psychosis, schizophrenia, schizoaffective disorders, mania, psychotic depression, affective disorders, dementia, anxiety, sleep disorders, appetite disorders, bipolar disorder, psychosis secondary to hypertension, migraine, vasospasm, and ischemia, motor tics, tremor, psychomotor slowing, bradykinesia, and neuropathic pain by administering a compound of Formula IV.

Another embodiment is a method for the treatment of neurodegenerative diseases, including Parkinson's disease, Huntington's disease, Alzheimer's disease, Spinocerebellar Atrophy, Tourette's Syndrome, Friedrich's Ataxia, Machado-Joseph's disease, Lewy Body Dementia, Dystonia, Progressive Supranuclear Palsy, and Frontotemporal Dementia by administering a compound of Formula IV.

Another embodiment is a method for treating dyskinesia associated with dopaminergic therapy, by administering a compound of Formula IV.

Another embodiment is a method for treating dystonia, myoclonus, or tremor associated with dopaminergic therapy, by administering a compound of Formula IV.

Another embodiment is a method for treating a thrombotic condition including myocardial infarction, thrombotic or ischemic stroke, idiopathic and thrombotic thrombocytopenic purpura, peripheral vascular disease, and Raynaud's disease, by administering a compound of Formula IV.

Another embodiment is a method of treating addiction, including alcohol addiction, opioid addiction, and nicotine addiction, by administering a compound of Formula IV.

Another embodiment is a method of treating a decrease in libido or ejaculatory problems by administering a compound of Formula IV.

EXAMPLES

Experimental Procedures

Powder X-ray Diffraction (PXRD): PXRD was performed on a Philips 1710 powder X-ray diffractometer using CuK$_\alpha$ radiation. d-spacings were calculated from the 2θ values using the wavelength of 1.54060 Å. Generally, 2θ values were within an error of ±0.1-0.2°. The experimental error on the d-spacing values was therefore dependent on the peak location.

Differential Scanning Calorimetry (DSC): Perkin Elmer DSC 7 in gold sample pan sealed under nitrogen for characterization of form A and sealed under about 50% relative humidity for characterization of form B. Heating rate 10 K/min. All melting points were obtained from the peak temperatures of the DSC measurements, rather than onset temperatures.

FT-Raman Spectroscopy: Bruker RFS100. Nd:YAG 1064 nm excitation, 100 mW laser power, Ge-detector, 64 scans, range 25-3500 cm$^{-1}$, 2 cm$^{-1}$ resolution:

TG-FTIR: Thermogravimetric measurements were carried out with a Netzsch Thermo-Microbalance TG 209 coupled to a Bruker FTIR Spectrometer Vector 22 (sample pans with pinhole, nitrogen atmosphere, heating rate 10K/min).

HPLC: HPLC measurements were carried out with a HP LC1090M, Column Symmetry C18, 3.0.150 mm.

Example 1

Preparation of N-(4-fluorobenzyl)-N-(1-methylpiperidin-4-yl)-N'-(4-(2-methylpropyloxy)phenylmethyl)carbamide a) Preparation of

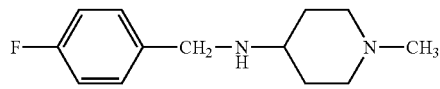

Triacetoxy borohydride (6.5 kg) was added over 1.5 h to a solution of N-methylpiperid-4-one (3.17 kg) and 4-fluorobenzylamine (3.50 kg) in methanol (30 L) maintaining the temperature under 27° C. The reaction mixture was stirred for 15 h at 22° C. The residual amine was checked by gel chromatography (4-fluorobenzylamine: <5%). A solution of 30% sodium hydroxide (12.1 kg) in water (13.6 kg) was added in 75 minutes (min) maintaining the temperature under 20° C. Methanol was distilled off to a residual volume of 26 litres. Ethyl acetate was added (26 L), the solution was stirred for 15 min, the phases were decanted over 15 min and the lower aqueous phase was discarded. Ethyl acetate was distilled under reduced pressure from the organic phase at 73-127° C.

At this stage the residue was mixed with a second crude batch prepared according to this method. The combined products were then distilled at 139-140° C./20 mbar to yield 11.2 kg product (>82%).

b) Preparation of

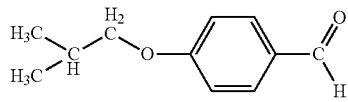

4-Hydroxybenzaldehyde (4.0 kg) and ethanol (20 L) were added to a solution of isobutyl bromide (9.0 kg) in ethanol (15 L). Potassium carbonate (13.6 kg) was added and the suspension was refluxed (74-78° C.) for 5 days. The residual 4-hydroxybenzaldehyde was checked by HPLC (<10%). The suspension was cooled to 20° C. and used in the next step.

c) Preparation of

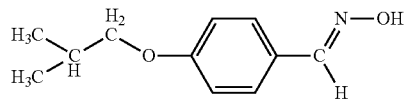

Hydroxylamine (50% in water, 8.7 kg) was added to the product from previous step b) (174 L, 176 kg) and ethanol (54 L). The suspension was refluxed (77° C.) for 3 h. Unreacted residual was checked by HPLC (<5%). The suspension was cooled to 30° C., filtered and the filter was washed with ethanol (54 L). The solution was concentrated by distillation under reduced pressure at 30° C. to a residual volume of 67 litters. The solution was cooled to 25° C. and water (110 L) was added. The suspension was concentrated by distillation under reduced pressure at 30° C. to a residual volume of 102 litters. Petrol ether (60-90 fraction, 96 L) was added and the mixture was heated to reflux (70° C.). The solution was cooled to 40° C. and crystallization was initiated by seeding. The suspension was cooled to 5° C. and stirred for 4 h. The product was centrifuged and the cake was washed with petrol ether (60-90 fraction, 32 L). The wet cake was dried at about 40° C. to yield 16 kg product (63%).

d) Preparation of

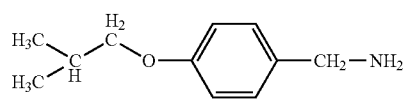

The product from previous step c) (15.7 kg) was dissolved in ethanol (123 L). Acetic acid (8.2 kg) and palladium on charcoal 5% wet (1.1 kg) were added. The oxime was hydrogenated at 22° C. and 1.5 bar for 4 h. Consumption of oxime was checked by HPLC. The catalyst was filtered and the solvent was distilled under reduced pressure at 36° C. to a final volume of 31 L. Ethyl acetate (63 L) was added and the mixture was heated to reflux (75° C.) until dissolution. The solution was cooled to 45° C. and the crystallization was initiated by seeding. The suspension was cooled to 6-10° C. and stirred for 2.5 h. The product was centrifuged and the cake was washed with 2 portions of ethyl acetate (2×0.8 L). The wet cake was dried at a temperature of about 40° C. to yield 8 kg (41%).

e) Preparation of

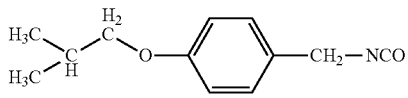

Aqueous sodium hydroxide (30%, 5.0 kg) was added to a suspension of the product from previous step d) (7.9 kg) in heptane (41 L). The solution was heated to 47° C., stirred for 15 min and decanted over 15 min. The pH was checked (pH>12) and the aqueous phase was separated. The solvent was removed by distillation under reduced pressure at 47-65° C. Heptane was added (15 L) and then removed by distillation under reduced pressure at 58-65° C. Heptane was added (7 L), the solution was filtered, and the filter was washed with heptane (7 L). The solvent was removed by distillation under reduced pressure at 28-60° C. Tetrahydrofuran (THF, 107 L) and triethylamine (TEA, 6.8 kg) were added and the temperature was fixed at 22° C. In another reactor, phosgene (5.0 kg) was introduced in tetrahydrofuran (88 L) previously cooled to −3° C. The THF and TEA solution was added to the solution of phosgene in 3 h 50 min, maintaining the temperature at −3° C. The reactor was washed with tetrahydrofuran (22 L). The mixture was stirred for 45 min at 20° C. and then for 90 min at reflux (65° C.). The solvent was distilled under reduced pressure at 25-30° C. to a residual volume of 149 L. The absence of phosgene was controlled. At this stage, phosgene was still present and the suspension was degassed by bubbling nitrogen through it. After this operation, the level of phosgene above the solution was below 0.075 ppm. The suspension was filtered and washed with tetrahydrofuran (30 L). The solvent was distilled under reduced pressure at 20-25° C. to a residual volume of 40 L. Tetrahydrofuran (51 L) was added and the solvent was distilled under reduced pressure at 20-25° C. to a residual volume of 40 L. The final volume was adjusted to about 52 litters by addition of tetrahydrofuran (11 L). The solution was analysed and used in the next step.

f) Preparation of the Title Compound of Formula I

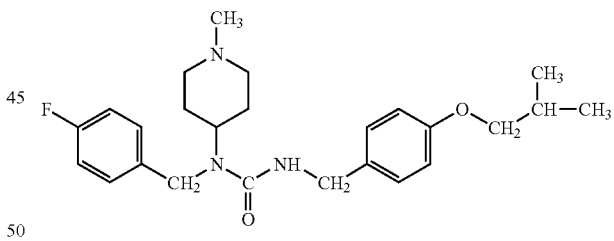

The product from previous step e) (51 L) was added in 1 h to a solution of the product from step a) (7.3 kg) in tetrahydrofuran (132 L) at 17° C. The line was washed with tetrahydrofuran (12 L) and the mixture was stirred for 15 h. Residual product from the first step was checked by HPLC. The solvent was removed by distillation under reduced pressure at 20-38° C. to a residual volume of 165 L. Charcoal (Norit SX1-G, 0.7 kg) was added, the mixture was stirred for 15 min and filtered. The line was washed with tetrahydrofuran (7 L) and the solvent was removed by distillation under reduced pressure at 20-25° C. to a residual volume of 30 L. Isopropyl acetate (96 L) was added to obtain a solution of the title compound of formula I, which contains a small amount of impurities (mainly side products from the previous reactions.) Removal of the solvent from a sample yields a substantially amorphous solid.

The solution with the crude product was used for the direct preparation of the hemi-tartrate and simultaneously for the purification of the free base via the hemi-tartrate through crystallization from suitable solvents.

Example 2

Preparation of Pure Crystalline Form Y of Compound of Formula I 15.78 g of the tartrate salt prepared according to Example 10 described below was dissolved in 130 ml water. 500 ml TBME was added and the pH adjusted to 9.8 by addition of 2 N NaOH solution. After precipitation of a white solid, the aqueous phase was extracted 5 times by 500 ml TBME. The organic phases were concentrated until a volume of about 400 ml remains. The solution was stored at 6° C. The precipitate was filtered, washed with TBME and finally dried in vacuum for 5 hours. Yield: 8.24 g of a white powder. The mother liquor was concentrated to a fourth and stored at 6° C. The precipitate was filtered and dried in vacuum for 18 hours. Yield: 1.6 g of a white powder.

PXRD revealed a crystalline sample. The powder X-ray diffraction pattern is shown in FIG. 1 and the characteristic peaks in 2 theta with the corresponding d-spacing values in Å are given in Table 1. Raman spectroscopy also indicated a crystalline sample. No Raman peaks from tartaric acid were found. TG-FTIR revealed a mass loss of about 0.4% between 60° C. and 150° C., believed to be caused by the liberation of TBME. Above about 190° C., the sample started to decompose. DSC (−50° C. to 210° C., 10° C./min) revealed a melting endotherm at 124° C.

TABLE 1 d-Spacings for crystal form Y (free base)

| Angle [°2θ] | d-spacings [Å] | Intensity (qualitative) |
| --- | --- | --- |
| 6.8 | 13.0 | vs |
| 8.1 | 10.9 | vs |
| 13.0 | 6.8 | vw |
| 13.7 | 6.5 | s |
| 14.4 | 6.2 | w |
| 17.0 | 5.2 | w |
| 19.1 | 4.7 | m |
| 19.7 | 4.5 | w |
| 20.8 | 4.3 | s |
| 21.0 | 4.22 | vs |
| 22.2 | 4.00 | m |
| 25.2 | 3.53 | vw |
| 26.2 | 3.40 | vw |
| 27.1 | 3.28 | w |
| 27.5 | 3.24 | w |
| 27.9 | 3.19 | w |
| 29.0 | 3.08 | w |
| 30.7 | 2.91 | w |
| 33.0 | 2.72 | w |

Approximate solubility of the free base was determined at room temperature for 11 solvents as listed in Table 2.

TABLE 2

Approximate solubility of the crystalline free base of formula I in various solvents

| Solvent | Solubility (mg/ml) |
| --- | --- |
| acetone | 100 |
| ethanol | 260 |
| ethyl acetate | <30 |

TABLE 2-continued

Approximate solubility of the crystalline free base of formula I in various solvents

| Solvent | Solubility (mg/ml) |
| --- | --- |
| isopropanol | 100 |
| tetrahydrofuran | >250 |
| acetonitrile | <50 |
| dichloromethane | >500 |
| 1,4-dioxane | 140 |
| methanol | 170 |
| toluene | <70 |
| water | <4 |

Example 3

Preparation of the Hemi-Tartrate of Formula Iv from the Solution Obtained in Example 1(f)

a) Crude Product Salt Formation

To the solution of the compound of Formula I in isopropyl acetate (96 L) according to Example 1(f) was added at 23° C. a previously prepared solution of tartaric acid (1.7 kg) in water (1.7 L) and tetrahydrofuran (23 L). The residual suspension was stirred for 2.5 days at 22° C. The tartrate crude product was centrifuged and the cake was washed with 4 portions of isopropyl acetate (4×23 L). A total of 107 kg of mother liquors was saved for later use in obtaining the tartrate salt. The wet cake was dried at about 40° C. to yield 8.3 kg (50%) product.

b) Purification

The tartrate crude product of previous step a) (8.1 kg) was dissolved in demineralized water (41 L) at 22° C. Isopropyl acetate (40 L), 30% aqueous sodium hydroxide (4.3 kg) and sodium chloride (2 kg) were added. The pH was checked (>12) and the solution was stirred for 15 min. The solution was decanted over 15 min and the aqueous phase was separated. The aqueous phase was re-extracted with isopropyl acetate (12 L). Demineralized water (20 L) and sodium chloride (2.0 kg) were added to the combined organic phases, the solution was stirred for 15 min, decanted over 15 min and the aqueous phase was discarded. Charcoal (0.4 kg) was added and the mixture was stirred for 20 min and filtered. After a line wash with isopropyl acetate (12 L), the solvent was removed under reduced pressure at 20-25° C. Heptane (49 L) was added and the suspension was stirred for 15 min at 40° C. Then, 8 L of solvent was removed by distillation under reduced pressure at 38-41° C. The slurry was cooled to 20° C. and stirred for 1 h. The product was centrifuged and the cake was washed with heptane (5 L). The wet compound of Formula I (5.5 kg) was dissolved in ethanol (28 L) at 45° C. A solution of tartaric acid (0.72 kg) in ethanol (11 L) was added at 45° C. and the line was washed with ethanol (9 L). The solution was cooled to 43° C., seeded with the tartrate salt of the compound of Formula I, then the slurry was cooled to 35° C. in 30 min, stirred at this temperature for 1 h and cooled to −5° C. After 14 h at this temperature the product was centrifuged and washed with two portions of ethanol (2×6 L). A total of 42 kg of mother liquors were saved for later use in obtaining the tartrate salt. The wet cake was dried at about 45° C. for 76 h to yield 4 kg.

c) Additional Isolation from Mother Liquors

Additional product was obtained from the saved mother liquors as follows. The solvent was removed by distillation under reduced pressure at 24-26° C. from a solution of the crude tartrate mother liquors (107 kg) from step a) and the Formula I-tartrate mother liquors (42 kg) from step b) to a residual volume of 27 L. Demineralized water (25 L) was added and the mixture was concentrated to a residual volume of 32 L by distillation under reduced pressure at 24-26° C. Isopropyl acetate (30 L) and 30% aqueous sodium hydroxide (2.7 kg) were added. The pH was checked (>12) and the solution was stirred for 15 min. The solution was decanted over 15 min and the aqueous phase was separated. The aqueous phase was re-extracted with isopropyl acetate (6 L). Demineralized water (9 L) and sodium chloride (0.9 kg) were added to the combined organic phases, the solution was stirred for 15 min, decanted over 15 min and the aqueous phase was discarded. Charcoal (0.3 kg) was added, the mixture was stirred for 20 min and filtered. After a line wash with isopropyl acetate (8 L), the solvent was removed by distillation under reduced pressure at 20-25° C. to a residual volume of 12 L, but not to dryness. Heptane (25 L) was added at 30° C., the slurry was cooled to 20° C. and stirred for 1.5 h. The product was centrifuged and the cake was washed with heptane (2×5 L). The wet cake (4.3 kg) was dissolved in ethanol (23 L) at 45° C. A solution of tartaric acid (0.58 kg) in ethanol (7.5 L) was added at 45° C. and the line was washed with ethanol (6 L). The solution was stirred for 20 min (crystallization of the product) and the slurry was cooled to 35° C. in 30 min, stirred at this temperature for 1 h and cooled to −5° C. After 14 h at this temperature the product was centrifuged and washed with two portions of ethanol (2×4 L). The wet cake was dried at about 45° C. for 80 h giving 3.3 kg of product.

PXRD of both products revealed a crystalline sample and the high baseline indicated the presence of amorphous parts and possibly of small amounts of crystalline form C. PXRD reveals that the solid product contains substantially crystalline form A of N-(4-fluorobenzyl)-N-(1-methylpiperidin-4-yl)-N'-(4-(2-methylpropyloxy)phenylmethyl) carbamide hemi-tartrate of formula IV. Crystalline form A contains some water as demonstrated when subjected to heat in thermogravimetric analysis (TG-FTIR, loss of 2.2% attributed to water and a small amount of solvent). The amount indicates that crystalline form A was a hemi-hydrate (theoretical value of water content 1.8%). However, water was only weakly bound, since the weight loss starts just above ambient temperature and was complete at about 150° C. The water can also easily be removed by treatment with dry nitrogen for a longer time (about up to 20 hours). The melting point of the dehydrated form A was about 133-135° C. with an enthalpy of fusion of about 70 J/g (peak temperature, measured by DSC). Form A shows a considerable water uptake when exposed to humidity above 75% relative humidity. The water was given off when the relative humidity was decreased to 50% and less. This behaviour was typical for a deliquescent solid.

Approximate solubility was measured by preparation of saturated solutions in various solvents and gravimetric determination of dissolved substance after solvent removal. The results are given in Table 3.

TABLE 3

Approximate solubility of the crystalline form A of compound of formula IV

| Solvent | Solubility (mg/ml) |
| --- | --- |
| 1,4-dioxane | ~2 |
| 2-propanol | ~1 |
| acetone | ~2 |
| acetone/water (1:1) | >200 |
| acetonitrile | ~2 |
| dichloromethane | >30 |

TABLE 3-continued

Approximate solubility of the crystalline form A of compound of formula IV

| Solvent | Solubility (mg/ml) |
| --- | --- |
| dimethylsulfoxide | >200 |
| ethanol | >10 |
| ethyl acetate | <1 |
| 2-propanol/water (9:1) | <1 |
| methanol | >100 |
| methyl ethyl ketone | <1 |
| t-butyl methyl ether | <1 |
| tetrahydrofuran | >5 |
| toluene | <1 |
| water | >300 |

Example 4

Preparation of the Hemi-Tartrate of Formula Iv from Crude Free Base of Formula I Crude product from Example 1(f) (5.5 kg) was dissolved at 45° C. in ethanol (28 L). A solution of (+)-L-tartaric acid (0.72 kg) in ethanol was added at 45° C. and the line was washed with 9 L of ethanol. The solution was cooled to 43° C. and seeded with the hemi-tartrate of formula IV. The slurry was then cooled to 35° C. over 30 min, stirred at this temperature for 1 hour and cooled under stirring to −5° C. After 14 hours stirring at this temperature, the product was centrifuged and washed with 2 portions of ethanol (2×6 L). The wet cake was dried at 45° C. for 76 hours yielding 4.0 kg of product (83%, based on tartaric acid). PXRD of the product revealed that polymorph A was formed.

Example 5

Preparation of the Hemi-Tartrate of Formula Iv from Crude Free Base of Formula I Crude product according to Example 1(f) (4.3 kg) was dissolved at 45° C. in ethanol (23 L). A solution of (+)-L-tartaric acid (0.58 kg) in ethanol was added at 45° C. and the line was washed with 6 L of ethanol. The solution was stirred for 20 min (formation of solid precipitate) and the slurry was cooled to 35° C. over 30 min. The slurry was stirred at this temperature for 1 hour and then cooled to −5° C. After 14 hours stirring at this temperature, the product was centrifuged and washed with 2 portions of ethanol (2×4 L). The wet cake was dried at 45° C. for 80 hours yielding 3.3 kg of product (85%, based on tartaric acid). PXRD of the product revealed that polymorph A was formed.

Example 6

Preparation of Amorphous Form of Compound of Formula IV Through Lyophilization of Aqueous Solution 2.02 g of crude free base of formula I was dissolved at room temperature in 8.0 ml water (Fluka no. 95306) at 23±2° C. The obtained solution was filtered through a 0.22 μm millipore filtration unit, and the filtered solution was transferred into a 100 ml round glass flask. The clear solution was frozen in a bed of dry ice (solid $CO_2$) at −78° C., and subsequently the glass flask with the frozen solution was connected to a lyophilizer. Lyophilizer type: CHRIST, BETA 2-8 LD-2. The initial pressure of was about 0.10 mbar, and the cold trap temperature was −82° C., and the end pressure was 0.007 mbar. After about 15 hours, the lyophilization was complete and the flask was disconnected. The obtained white solid powder was characterized by differential scanning calorimetry and powder X-ray diffraction. PXRD for the obtained product shows the complete amorphous state, and likewise DSC measurement reveals a completely amorphous compound with a glass transition temperature near 54° C. and a $\Delta C_p$ of about 0.5 J/g/° C.

Example 7

Preparation of Crystalline Pure Form a by Re-Crystallization 142.5 g of the product from Example 5 was suspended in absolute ethanol (750 ml). The white suspension was heated under stirring over 30 min to 70° C. From 60° C., the solution was clear yellowish. The solution was slowly cooled and the product started to crystallize at about 48° C. Cooling from 48° C. to 15° C. was performed over 4 h. The suspension was stirred for 1.5 h at 15° C. Thereafter, a thick suspension was formed. The precipitate was filtered under vacuum, washed twice with 70 ml absolute ethanol and then dried in vacuum at 40° C. The dry weight was 135.2 g (95% yield).

This product was again suspended under stirring in 850 ml absolute ethanol and heated over 30 min to 75° C. The dissolution was complete and the solution was substantially colourless from 58-60° C. The solution was filtered at 75° C., the line was washed with 50 ml absolute ethanol, and the solution was then allowed to cool under stirring. Crystallization initiated at 48° C. The product crystallized at about 42-44° C. and a voluminous precipitate was formed. The suspension was allowed to cool over night to room temperature. The suspension was filtered at 20-22° C. and washed twice with 50 ml absolute ethanol. The white and solid product was dried over 48 h under vacuum at 42° C. The dry weight was 123.6 g (92% yield).

The X-ray powder diffraction pattern is shown in FIG. 2 and the characteristic peaks in 2 theta with the corresponding d-spacing values in Å are given in Table 4.

TABLE 4 d-Spacings for the crystalline form A of the compound of formula IV

| Angle [°2θ] | d-spacings [Å] | Intensity (qualitative) |
| --- | --- | --- |
| 4.7 | 18.6 | s |
| 5.3 | 16.7 | vs |
| 8.7 | 10.2 | s |
| 10.8 | 8.2 | m |
| 11.5 | 7.7 | w |
| 12.0 | 7.4 | w |
| 13.6 | 6.5 | w |
| 14.3 | 6.2 | m |
| 14.6 | 6.1 | vs |
| 15.1 | 5.86 | w |
| 17.2 | 5.14 | m |
| 17.6 | 5.03 | m |
| 18.6 | 4.78 | m |
| 18.9 | 4.69 | m |
| 19.1 | 4.63 | s |
| 19.8 | 4.49 | s |
| 20.0 | 4.44 | vs |
| 20.4 | 4.35 | m |
| 21.6 | 4.10 | m |
| 22.4 | 3.96 | s |
| 24.3 | 3.66 | m |
| 25.7 | 3.47 | w |
| 26.6 | 3.35 | w |
| 29.3 | 3.05 | w |

Example 8

Preparation of Crystalline Pure Form A by Re-Crystallization 105.0 g compound of formula IV as obtained in Example 5 was dissolved under stirring at 65° C. in 560 ml absolute ethanol and then cooled under stirring to 48° C. at a cooling rate of 1° C./min. Crystallization started after a few minutes at this temperature and the suspension turned to a thick paste within 1 h. The suspension was heated again to 60° C. and then cooled to 48° C. at a rate of 1° C./min. The obtained suspension was stirred and cooled to 15° C. at a cooling rate of 3° C./h. The crystalline precipitate was separated by filtration and the bottle was washed with 50 ml absolute ethanol cooled to 5° C. The crystalline residue was then dried in air at 30° C. for 18 h and thereafter under vacuum and room temperature for 40 hours to yield 98.1 g crystalline product. PXRD indicated that the product was polymorph A. TG-FTIR shows a weight loss of about 2.5%, which was attributed to water and a small amount of ethanol.

Example 9

Preparation of Crystalline Pure Form A by Re-Crystallization 21.0 g compound of formula IV as obtained in Example 3(b) was dissolved under stirring at 65° C. in 112 ml absolute ethanol and then cooled under stirring to 48° C. at a cooling rate of 1° C./min. Crystallization started after a few minutes at this temperature and the suspension turned to a thick paste within 1 h. The suspension was heated again to 60° C. and then cooled to 48° C. at a rate of 1° C./min. The obtained suspension was stirred and cooled to 15° C. at a cooling rate of 3° C./h. The crystalline precipitate was separated by filtration and the bottle was washed with 10 ml absolute isopropanol cooled to 5° C. The crystalline residue was first dried under nitrogen at 25° C. for 18 h and thereafter under vacuum and room temperature for 20 hours to yield 19.9 g crystalline product. PXRD indicated that the produce was polymorph A with similarities to form D. TG-FTIR showed a weight loss of about 7.7%, which was attributed to isopropanol and water. The product was again dried at 30° C. in air for 20 h yielding a product with a weight loss of about 5% isopropanol and water.

Example 10

Preparation of Crystalline Pure Form A by Re-Crystallization 150.0 g compound of formula IV as obtained in Example 3(b) was dissolved under stirring at 65° C. in 112 ml absolute ethanol and then cooled under stirring to 48° C. at a cooling rate of 1° C./min. Crystallization started after a few minutes at this temperature and the suspension turned to a thick paste within 1 h. The suspension was heated again to 60° C. and then cooled to 48° C. at a rate of 1° C./min. The obtained suspension was stirred and was cooled to 15° C. at a cooling rate of 3° C./h. The crystalline precipitate was separated by filtration and the bottle was washed with 10 ml absolute ethanol cooled to 5° C. The crystalline residue was first dried under vacuum and 40° C. for 50 hours to yield 146 g crystalline product, which was according to PXRD pure polymorph A.

Example 11

Preparation of Crystalline Pure Form A by Suspension Equilibration 20 mg of the compound of formula IV from Example 3(b) was suspended in a solvent and stirred for 4 days at a variable temperature with cycling from 18 to 40° C. The product was identified as crystalline form A by PXRD or Raman spectroscopy when using the following solvents: ethanol, isopropanol, heptane, methyl ethyl ether, t-butyl methyl ether (TBME), ethanol and TBME, ethanol/heptane, TBME saturated with water.

Example 12

Preparation of Crystalline Pure Form A by Suspension Equilibration from Amorphous Form 64 mg of amorphous compound from Example 6 was suspended in 1.0 ml tetrahydrofuran and stirred at 5° C. for 18 hours. The solid was filtered and dried under nitrogen at room temperature for 2 hours. Crystalline form A was identified by PXRD or Raman spectroscopy.

Example 13

Preparation of Crystalline Pure Form A by Suspension Equilibration from Amorphous Form 20 mg amorphous compound from Example 6 was suspended in 500 ethanol/acetone (1:1) and then stirred for 3 days with cycling from room temperature to 40° C. Crystalline form A was identified by Raman spectroscopy.

Example 14

Preparation of Crystalline Pure Form A by Suspension Equilibration from Amorphous Form 20 mg amorphous compound from Example 6 was suspended in 500 µl tetrahydrofuran and then stirred for 3 days with cycling from room temperature to 40° C. Crystalline form A was identified by Raman spectroscopy.

Example 15

Preparation of Crystal Form B by Precipitation with Anti-Solvent Methyl Ethyl Ketone 600 µl of an aqueous solution containing about 160 mg of the compound of formula IV from Example 3(b) was added to 10 ml methyl ethyl ketone (MEK) at 5° C. The suspension was stirred for 3 days. 5 ml MEK was added and stirring was continued for 5 hours. The solid was filtered off and dried in air for at room temperature for 12 h. Crystalline form B was identified by XPRD or Raman spectroscopy. TG-FTIR shows a weight loss of about 2.5%, which was attributed to water. The X-ray powder diffraction pattern is shown in FIG. 3 and the characteristic peaks in 2 theta with the corresponding d-spacing values in Å are given in Table 5.

TABLE 5 d-Spacings for the crystalline form B of the compound of formula IV

| Angle [°2θ] | d-spacings [Å] | Intensity (qualitative) |
| --- | --- | --- |
| 5.1 | 17.4 | vs |
| 8.7 | 10.2 | s |
| 10.0 | 8.8 | w |
| 13.7 | 6.4 | w |
| 15.0 | 5.91 | vs |
| 16.2 | 5.46 | w |
| 17.8 | 4.99 | m |
| 18.1 | 4.90 | m |
| 19.2 | 4.62 | m |
| 19.7 | 4.50 | vs |
| 20.3 | 4.37 | vs |
| 21.1 | 4.20 | w |
| 23.0 | 3.87 | vs |
| 23.8 | 3.73 | w |
| 24.8 | 3.58 | m |
| 26.1 | 3.42 | w |
| 30.8 | 2.90 | w |

Example 16

Preparation of Crystal Form B by Precipitation with Anti-Solvent Heptane 2.0 ml of a solution containing 135 mg of the compound of formula IV according to Example 3(b) in methylene chloride was added at room temperature to 3.0 ml heptane. The formed suspension was stirred for 24 h, then filtered off and dried in air at room temperature for 8 h. Crystalline form B was identified by PXRD or Raman spectroscopy. DSC measurement revealed a melting point of about 131° C. with a melting enthalpy of about 63 J/g.

Example 17

Preparation of Crystal Form B by Precipitation with Anti-Solvent Toluene 2.0 ml of a solution containing 135 mg of the compound of formula IV from Example 3(b) in methylene chloride was added at room temperature to 3.0 ml toluene. The formed suspension was stirred for 24 h, then filtered off and dried in air at room temperature for 14 h. Crystalline form B was identified by PXRD or Raman spectroscopy. DSC measurement revealed a melting point of near 129° C. with a melting enthalpy of about 71 J/g.

Example 18

Preparation of Crystal Form B by Precipitation with Anti-Solvent Acetonitrile 2.0 ml of a solution containing 135 mg of the compound of formula IV from Example 3(b) in methylene chloride was added at room temperature to 3.0 ml acetonitrile. The formed suspension was stirred for 24 h, then filtered off and dried in air at room temperature for 18 h. Crystalline form B was identified by Raman spectroscopy.

Example 19

Preparation of Crystal Form B by Precipitation with Anti-Solvent Ethyl Acetate 1.5 ml of a solution containing 210 mg of the compound of formula IV according to Example 3(b) in methanol was added at room temperature to 10 ml ethyl acetate. No product precipitated until about 50% of ethyl acetate/methanol solvent mixture was evaporated at room temperature. The resulting suspension was stirred at 15° C. for 18 h, then filtered off and dried in air at room temperature for 12 h. Crystalline form B was identified by Raman spectroscopy.

Example 20

Preparation of Crystal Form B by Suspension Equilibration with Polymorph A in Acetonitrile 20 mg of the compound of formula IV from Example 3(b) was suspended in acetonitrile and stirred for 4 days at a temperature cycling from 18 to 40° C., then filtered off and dried in air at room temperature for 18 h. Crystalline form B was identified by Raman spectroscopy.

Example 21

Preparation of Crystal Form B by Suspension Equilibration with Polymorph A in ethyl acetate 20 mg of the compound of formula IV from Example 3(b) was suspended in 6 ml ethyl acetate and stirred for 4 days at a temperature cycling from 18 to 40° C., then filtered and dried in air at room temperature for 18 h. Crystalline form B was identified by Raman spectroscopy.

Example 22

Preparation of Crystal Form B by Suspension Equilibration with Polymorph A in Ethanol/MEK 20 mg of the compound of formula IV from Example 3(b) was suspended in 5 ml ethanol/MEK (1:1) and stirred for 4 days at a temperature cycling from 18 to 40° C., then filtered and dried in air at room temperature for 18 h. Crystalline form B was identified by Raman spectroscopy.

Example 23

Preparation of Crystal Form B by Suspension Equilibration with Polymorph A in Water Saturated Ethyl Acetate 20 mg of the material from Example 6 was suspended in 500 µl ethyl acetate saturated with water and stirred for 3 days at a temperature cycling from room temperature to 40° C., then filtered and dried in air at room temperature for 8 h. Crystalline form B was identified by Raman spectroscopy.

Example 24

Preparation of Crystal Form B by Suspension Equilibration with Polymorph A in Acetonitile Containing 1% Water 20 mg of the material from Example 6 was suspended in 500 µl acetonitrile containing 1% water and stirred for 3 days at a temperature cycling from room temperature to 40° C., then filtered and dried in air at room temperature for 16 h. Crystalline form B was identified by Raman spectroscopy.

Example 25

Preparation of Crystal Form B by Suspension Equilibration with Polymorph A in Ethyl Acetate/Water 1.0 g of the material from Example 6 was suspended in 10 ml ethyl acetate and 100 ml water and stirred for 100 h at room temperature, then filtered off and dried in air at room temperature for 18 h. 750 mg of crystalline form B was obtained as identified by Raman spectroscopy and powder X-ray diffraction.

Example 26

Preparation of Crystal Form B by Suspension Equilibration with Polymorph A in Ethanol/MEK 20 mg of the compound of formula I from Example 3(b) was suspended in 7 ml ethanol/MEK (1:1) and stirred for 4 days at a temperature cycling from 18 to 40° C., then filtered and dried in air at room temperature for 18 h. Crystalline form B was identified by Raman spectroscopy.

Example 27

Preparation of Crystal Form B by Suspension Equilibration with Amorphous Form in Heptane 60 mg of the material from Example 6 was suspended in 1.0 ml heptane and stirred at 40° C. for 18 h. The solid was filtered and dried in air at 40° C. for 1 h. Crystalline form B was identified by Raman spectroscopy.

Example 28

Preparation of Crystal Form B by Suspension Equilibration with Amorphous Form in Ethyl Acetate 62 mg of the material from Example 6 was suspended in 1.0 ml ethyl acetate and stirred at 40° C. for 18 h. The solid was filtered off and dried in air at 40° C. for 1 h. Crystalline form B was identified Raman spectroscopy.

Example 29

Preparation of Crystal Form B by Suspension Equilibration with Amorphous Form in Acetonitrile 62 mg of the material from Example 6 were suspended in 1.0 ml acetonitrile and stirred at 5° C. for 18 h. The solid was filtered off and dried in nitrogen at 22° C. for 2 h. Crystalline form B was identified by Raman spectroscopy.

Example 30

Preparation of Crystal Form B by Suspension Equilibration with Amorphous Form in MEK 149 mg of the material from Example 6 were suspended in 3.0 ml MEK and stirred at room temperature for 16 h. The solid was filtered off and dried in nitrogen at 22° C. for 30 min. Crystalline form B was identified by Raman spectroscopy.

Example 31

Preparation of Crystal Form B by Suspension Equilibration with Amorphous Form in Water Saturated Ethyl Acetate

20 mg of the material from Example 6 was suspended in 500 µl ethyl acetate saturated with water, stirred for 3 days at a temperature cycling from room temperature to 40° C., then filtered and dried in air at room temperature for 6 h. Crystalline form B was identified by Raman spectroscopy.

Example 32

Preparation of Crystal Form B by Suspension Equilibration with Amorphous Form in Water Containing Solvent Mixture

70 mg of the material from Example 6 was suspended in 2.0 ml ethyl acetate/ethanol containing 1% water, stirred for 1 day at a temperature cycling from 5° C. to room temperature. Stirring was then continued at 10° C. for 5 days. The solid was filtered off and dried in air at room temperature for 15 min. Crystalline form B was identified by Raman spectroscopy.

Example 33

Preparation of Crystalline Form C by Suspension Equilibration of Polymorph A in acetone

20 mg of the compound of formula IV from Example 3(b) was suspended in 1 ml acetone, and 2 mg of form C seeding crystals were added, and the suspension was agitated for 4 days at a temperature cycling from 18 to 40° C., then filtered and dried in air at room temperature for 1 h. Crystalline form C was identified by Raman spectroscopy.

Example 34

Preparation of Crystalline Form C by Suspension Equilibration of Polymorph A in Tetrahydrofuran (THF)

20 mg of the compound of formula IV from Example 3(b) was suspended in 500 µl THF, 2 mg of form C seeding crystals were added, and the suspension was agitated for 3 days at a temperature cycling from 18 to 40° C., filtered off, dried in air at room temperature for 3 h. Crystalline form C was identified by Raman spectroscopy.

Example 35

Preparation of Crystalline Form C by Suspension Equilibration of Polymorph A in Tetrahydrofuran (THF)

255 mg of the compound of formula I from Example 3(b) was suspended in 5.0 ml THF, 25 mg of form C was added as seeding crystals, and the suspension was stirred for 40 h at a temperature of 40° C., filtered, and dried under nitrogen at room temperature for 15 min. Crystalline form C was identified by PXRD and Raman spectroscopy.

Example 36

Preparation of Crystalline Form C by Suspension Equilibration of Polymorph A in Tetrahydrofuran (THF)

1.0 g of the compound of formula I from Example 3(b) was suspended in 6.0 ml THF, 50 mg of form C was added as seeding crystals, and the obtained suspension was stirred for 50 h at room temperature, filtered, and dried in air at room temperature for 45 min. Crystalline form C was identified by PXRD and Raman spectroscopy. TG-FTIR showed a weight loss of less than 0.9% below 150° C., which was attributed to water. Dynamic pour absorption experiments show that polymorph C does not absorb water, form a hydrate, are exhibit hygroscopicity. DSC experiments revealed a melting point near 177° C. with an enthalpy of fusion of about 129 J/g.

The X-ray powder diffraction pattern is shown in FIG. 4 and the characteristic peaks in 2 theta with the corresponding d-spacing values in A are given in Table 6.

TABLE 6 d-Spacings for the crystalline form C of the compound of formula IV

| Angle [°2θ] | d-spacings [Å] | Intensity (qualitative) |
|---|---|---|
| 7.3 | 12.0 | w |
| 8.2 | 10.7 | vs |
| 11.9 | 7.4 | vw |
| 12.8 | 6.9 | vw |
| 13.5 | 6.6 | vw |
| 14.3 | 6.2 | w |
| 15.1 | 5.86 | m |
| 16.0 | 5.53 | w |
| 16.8 | 5.28 | m |
| 17.2 | 5.16 | m |
| 18.3 | 4.84 | vs |
| 18.9 | 4.70 | m |
| 19.4 | 4.57 | s |
| 20.3 | 4.38 | m |
| 21.7 | 4.09 | w |
| 22.5 | 3.94 | w |
| 23.6 | 3.77 | s |
| 24.0 | 3.71 | m |
| 25.5 | 3.49 | w |
| 25.7 | 3.46 | w |
| 26.1 | 3.41 | w |
| 27.5 | 3.25 | vw |
| 29.0 | 3.08 | w |
| 30.5 | 2.93 | w |

Example 37

Preparation of Seeding Material of Polymorph C

25 g of compound of formula IV from Example 3(b) was suspended in 100 ml THF and the suspension was stirred for 3 days at 30° C. The solid was filtered off and dried under reduced pressure at 40° C. for 2 h. A yield of 23.3 g of pure polymorph C was obtained as confirmed by PXRD and Raman spectroscopy. The material was used as seeding crystals in later experiments.

Example 38

Preparation of Polymorph C

6.0 g of the crystalline material from Example 9 was suspended in 30 ml MEK and stirred at 50° C. 100 mg crystal seeds from Example 37 were added after 2 hours and stirring was continued for 80 hours at room temperature. The crystalline solid was filtered off and dried for 18 hours at 45° C. A yield of 4.7 g of polymorph C containing a small amount of polymorph A was obtained as confirmed by PXRD. TG-FTIR indicates no weight loss below 170° C.

Example 39

Preparation of Polymorph C 6.0 g of the crystalline material of Example 9 was suspended in 30 ml THF and stirred at 50° C. 100 mg crystal seeds from Example 37 were added after 2 hours and stirring was continued for 80 hours at room temperature. The crystalline solid was filtered off and dried for 18 hours at 45° C. A yield of 4.7 g of polymorph C containing a small amount of polymorph A was obtained as confirmed by PXRD. TG-FTIR indicates a weight loss of about 0.5% below 170° C., which was attributed to THF.

Example 40

Preparation of Polymorph C 6.0 g of the crystalline material of Example 8 was suspended in 40 ml THF and stirred at 50° C. 150 mg crystal seeds from Example 37 were added after 2 hours and stirring was continued for 104 hours at 40° C. A second portion of 200 mg crystal seeds from Example 37 was added after 30 hours The crystalline solid was filtered off and dried for 18 hours at 45° C. A yield of 5.0 g of polymorph C containing a small amount of polymorph A was obtained as confirmed by PXRD. TG-FTIR indicates a weight loss of about 0.5 to 0.8% below 170° C., which was attributed to THF.

Example 41

Preparation of Polymorph C 6.0 g of the crystalline material of Example 8 was suspended in 40 ml MEK and stirred at 50° C. 150 mg crystal seeds from Example 37 were added after 2 hours and stirring was continued for 104 hours at 40° C. A second portion of 200 mg crystal seeds from Example 37 was added after 30 hours. The crystalline solid was filtered off and dried for 18 hours at 45° C. A yield of 5.4 g of polymorph C containing a small amount of polymorph A was obtained as confirmed by PXRD. TG-FTIR indicates no weight loss below 170° C.

Example 42

Preparation of Pure Polymorph C 7.0 g of the crystalline material of Example 8 was suspended in 50 ml acetone and stirred at 50° C. 200 mg crystal seeds from Example 37 were added after 2 hours. A thick paste was formed and 10 ml acetone was added. Stirring was continued for 29 hours at 50° C. The suspension was then cooled to 10° C. and stirred at this temperature for 14 h. The crystalline solid was filtered off and dried in air for 4.5 hours at 45° C. yielding 6.3 g of pure polymorph C as confirmed by PXRD.

Example 42

Preparation of Pure Polymorph C 7.0 g of the crystalline material of Example 8 was suspended in 50 ml MEK and stirred at 60° C. 200 mg crystal seeds from Example 37 were added after 2 hours and stirring was continued for 29 hours at 60° C. The suspension was then cooled to 10° C. and stirred at this temperature for 14 h. The crystalline solid was filtered off and dried in air for 4.5 hours at 45° C. A yield of 6.0 g of pure polymorph C was obtained as confirmed by PXRD.

Example 43

Preparation of Pure Polymorph C 50.0 g of the crystalline material of Example 10 was suspended in 310 ml MEK and stirred (600 rpm) at 50° C. 1.5 g crystal seeds from Example 37 (suspension in 10 ml MEK) were added after 2 hours. Stirring was continued for 52 hours at 50° C. The suspension was then cooled to 15° C. and stirred at this temperature for 2 h. The crystalline solid was filtered off and dried under vacuum for 16 hours at 50° C. A yield of 44.2 g of pure polymorph C was obtained as confirmed by PXRD. TG-FTIR indicates no weight loss below 170° C. (solvent free product).

Example 44

Preparation of Pure Polymorph C 50.0 g of the crystalline material of Example 10 was suspended in 360 ml MEK and stirred (600 rpm) at 50° C. 1.5 g crystal seeds from Example 37 (suspension in 10 ml MEK) were added after 2 hours. Stirring was continued for 35.5 hours at 50° C. The suspension was then cooled to 15° C. and stirred at this temperature for 2 h. The crystalline solid was filtered off and dried under vacuum for 16 hours at 50° C. A yield of 41.5 g of pure polymorph C was obtained as confirmed by PXRD. TG-FTIR indicates no weight loss below 170° C. (solvent free product).

Example 45

Preparation of Pure Polymorph C from Solution in THF 7.0 g of the crystalline material of Example 10 was suspended in 35 ml THF and heated to 65° C. Crystal form A was completely dissolved, and the solution was cooled to 60° C. Then 0.35 g crystal seeds from Example 37 (suspension in 1.0 ml THF) were added and stirring was continued for about 30 minutes at 60° C. Thereafter, the suspension was cooled to 10° C. at a cooling rate of 0.15° C. per minute, and stirring was continued at this temperature for 2 h. The crystalline solid was filtered off and dried under vacuum for 16 hours at 50° C. A yield of 4.5 g of pure polymorph C was obtained as confirmed by PXRD and Raman spectroscopy.

Example 46

Preparation of Form C Directly from Solution 2.0 g of the crystalline material of Example 10 was suspended in 10 ml of THF at room temperature. Heating of the suspension to 65° C. led to a clear solution. This solution was cooled to 60° C. and 100 mg of seed crystals of form C from Example 37 were added to the solution. At this temperature, the suspension became slowly more concentrated, and after stirring this suspension for one hour at 60° C., the suspension was cooled to 10° C. at a rate of 10° C. per hour. After 5 hours, 10° C. was reached and stirring was continued overnight, about 14 hours, before the obtained solid was filtered off and dried at 50° C. for about 2 hours under vacuum to obtain pure crystalline form C.

Example 47

Stability Tests with Polymorph C a) Thermal Treatment

The compounds of Examples 3(b) (polymorph A), 25 (polymorph B), and 36 (polymorph C) were placed in sealed ampoules and exposed for 1 week to 100° C. Polymorphs A and B formed a deliquescent compact material, whereas polymorph C was substantially unchanged and remained a crystalline free flowing powder. The products where analyzed by HPLC and the purity was detected to indicate chemical stability via decomposition. Polymorph A showed a purity of 25.9%, polymorph B 28.3%, and polymorph C 99.7%, demonstrating the high stability of polymorph C.

Example 48

Exposure to Humidity

The compounds of Examples 3(b) (polymorph A), 25 (polymorph B), and 36 (polymorph C) were placed in open containers and exposed 1 week and 2 weeks at 60° C. and 75% relative humidity. In polymorph A, a water content of 2.8% was detected and the HPLC purity was 80%. Polymorph B transformed to polymorph C, a water content of 1.9% was detected, and the HPLC purity was 94.6%. Polymorph C remained unchanged and HPLC purity was 99.7%.

Example 49

Preparation of Crystalline Form E Using Polymorph A as Starting Material

600 µl of a solution containing 160 mg of compound of formula IV according to Example 3(b) in water was added at 5° C. to 10 ml isopropanol. A crystalline solid precipitated and the suspension was stirred for 5 hours at 5° C. The crystalline solid was filtered off and dried under nitrogen for 1 hour at room temperature. A yield of 164 mg of crystalline form D was obtained as confirmed by PXRD and Raman spectroscopy. TG-FTIR indicated a weight loss of about 8% below 170° C., which was attributed to isopropanol and water.

Example 50

Preparation of Crystalline Using E from Amorphous Form as Starting Material 200 mg of the material from Example 6 was suspended in 16.0 ml isopropanol. The suspension was stirred for 18 h at 40° C. and for 14 h at 20° C. The crystalline solid was filtered off and dried under nitrogen for 1 hour at room temperature. A yield of 178 mg of crystalline form D was obtained as confirmed by PXRD and Raman spectroscopy. TG-FTIR indicated a weight loss of about 6.6% below 170° C., which was attributed to isopropanol. The amount of isopropanol indicates existence of a hemi-solvate of isopropanol (theoretical content of isopropanol was 5.6%; solvent difficult to remove when drying).

The X-ray powder diffraction pattern is shown in FIG. 5 and the characteristic peaks in 2 theta with the corresponding d-spacing values in A is given in Table 7.

TABLE 7 d-Spacings for the crystalline form D of the compound of formula IV

| Angle [°2θ] | d-spacings [Å] | Intensity (qualitative) |
|---|---|---|
| 5.1 | 17.2 | s |
| 5.5 | 16.0 | m |
| 8.3 | 10.7 | vw |
| 9.0 | 9.8 | w |
| 13.4 | 6.6 | m |
| 14.5 | 6.1 | s |
| 14.8 | 6.00 | m |
| 15.5 | 5.73 | w |
| 16.6 | 5.33 | w |
| 17.1 | 5.17 | m |
| 18.1 | 4.91 | m |
| 19.1 | 4.64 | s |
| 19.5 | 4.54 | vs |
| 20.3 | 4.37 | vs |
| 21.7 | 4.10 | m |
| 22.7 | 3.91 | m |
| 23.2 | 3.84 | m |
| 24.2 | 3.67 | w |
| 25.1 | 3.55 | m |
| 26.0 | 3.42 | m |
| 26.9 | 3.32 | w |
| 28.5 | 3.13 | w |
| 29.2 | 3.06 | m |

Example 51

Preparation of Crystalline from E Using Amorphous Form as Starting Material 70 mg of the material from Example 6 was suspended in 1.0 ml t-butyl methyl ether (TBME). The suspension was stirred for 18 h at 40° C. The crystalline solid was filtered off and dried in air for 1 h at 40° C. A yield of 58 mg of crystalline form E was obtained as confirmed by PXRD and Raman spectroscopy.

Example 52

Preparation of Crystalline from Amorphous Form as Starting Material 150 mg of the material from Example 6 was suspended in 4.0 ml TBME. The suspension was stirred for 26 h at room temperature. The crystalline solid was filtered off and dried in air for 5 min at room temperature. A yield of 121 mg of crystalline form E was obtained as confirmed by PXRD and Raman spectroscopy. TG-FTIR (10° C./min) indicates a weight loss of about 5.1% starting above ambient temperature and being complete below 150° C., which was attributed to TBME. The amount of TBME indicates existence of a TBME-solvate.

The X-ray powder diffraction pattern is shown in FIG. 6 and the characteristic peaks in 2 theta with the corresponding d-spacing values in A are given in Table 8.

TABLE 8 d-Spacings for the crystalline form E of the compound of formula IV

| Angle [°2θ] | d-spacings [Å] | Intensity (qualitative) |
|---|---|---|
| 5.1 | 17.3 | vs |
| 5.5 | 16.2 | m |
| 8.4 | 10.6 | m |
| 9.0 | 9.8 | m |
| 10.9 | 8.1 | w |

TABLE 8-continued d-Spacings for the crystalline form E of the compound of formula IV

| Angle [°2θ] | d-spacings [Å] | Intensity (qualitative) |
|---|---|---|
| 11.8 | 7.5 | w |
| 13.5 | 6.6 | m |
| 14.7 | 6.0 | vs |
| 16.8 | 5.28 | m |
| 17.4 | 5.09 | s |
| 18.1 | 4.90 | m |
| 18.8 | 4.72 | vs |
| 19.7 | 4.51 | m |
| 20.2 | 4.39 | s |
| 20.8 | 4.26 | s |
| 22.0 | 4.04 | m |
| 23.0 | 3.86 | w |
| 24.0 | 3.70 | w |
| 25.2 | 3.54 | m |
| 25.6 | 3.48 | m |
| 29.6 | 3.02 | w |

Example 53

Preparation of Crystalline from F Amorphous Form as Starting Material 250 mg of the material from Example 6 was dissolved under stirring at 65° C. in 5.5 ml tetrahydrofuran (THF). The solution was cooled to 20° C., whereby a thick paste was formed. 3 ml THF was added and stirring was continued at 40° C. for 1 h. The suspension was then cooled to 20° C. and stirring continued for 3 h. The crystalline solid was filtered off and dried in air for 30 min at room temperature. A yield of 214 mg of crystalline form F was obtained as confirmed by PXRD and Raman spectroscopy. TG-FTIR (10° C./min) indicates a weight loss of about 3.0% starting above ambient temperature and being complete below 130° C., which was attributed to THF. The amount of THF indicates existence of a non-stoichiometric THF-solvate (theoretical content for mono-THF-solvate was 12.5% THF).

The X-ray powder diffraction pattern is shown in FIG. 7 and the characteristic peaks in 2 theta with the corresponding d-spacing values in Å are given in Table 8.

TABLE 9 d-Spacings for the crystalline form F of the compound of formula IV

| Angle [°2θ] | d-spacings [Å] | Intensity (qualitative) |
|---|---|---|
| 4.6 | 19.0 | w |
| 5.5 | 16.0 | m |
| 6.8 | 13.0 | m |
| 11.3 | 7.8 | w |
| 13.7 | 6.4 | m |
| 14.2 | 6.2 | m |
| 14.6 | 6.1 | w |
| 15.4 | 5.74 | w |
| 16.7 | 5.29 | w |
| 17.6 | 5.04 | m |
| 18.3 | 4.83 | m |
| 19.2 | 4.62 | m |
| 19.7 | 4.50 | m |
| 20.5 | 4.34 | m |
| 20.9 | 4.24 | vs |
| 21.9 | 4.05 | m |
| 22.8 | 3.89 | m |
| 23.7 | 3.76 | m |
| 24.9 | 3.58 | w |
| 27.2 | 3.27 | m |

Example 54

Preparation of N-(4-fluorobenzyl)-N-(1-methylpiperidin-4-yl)-N'-(4-(2-methylpropyloxy)phenylmethyl)carbamide hemi-tartrate a) Preparation of:

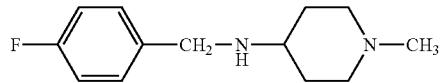

N-Methyl-4-piperidone (SM, 16.0 kg) and 4-Fluorobenzylamine (17.7 kg, 1.00 equivalents) were dissolved in methanol (110.2 kg, 8.70–v/w SM) at T=15-19° C., then 5% Palladium/C (0.59 kg, 3.68%–w/w SM) was added under nitrogen. The bulk was heated up to T=23-27° C. and hydrogenated at the same temperature and P=~5 bar until the hydrogen absorption stops (~11 hours). The residual SM was checked by GC (imine<5%), then the bulk was clarified (1575+GF92 filter papers) and the line was washed with methanol (5.1 kg, 0.40–v/w SM). The solvent was distilled under reduced pressure (P=265-60 mbar, T=35-40° C.) and the oily residue was purified by fractional distillation under vacuum at T=135-140° C., P=8-0.5 mbar to provide 22.15 kg (70%) of product.

b) Preparation of:

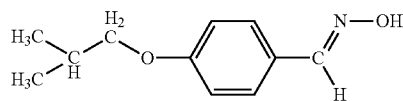

4-Hydroxybenzaldehyde (SM, 60.0 kg) was dissolved in dimethylformamide (142.5 kg, 2.50–v/w SM) at T=15-25° C., then solid potassium carbonate (137.2 kg, 2.02 equiv.) and potassium iodide (8.1 kg, 0.10 equiv.) were added portion wise at T<30° C. and the suspension heated up to T=78-82° C. The temperature of the condenser was fixed to 15° C. and isobutylbromide (134.8 kg, 2.00 equiv.) was added to the suspension over 4-5 hours at T=78-82° C. At the end of the addition, the mixture was stirred ~3 hours at T=78-82° C. and residual SM was checked by HPLC (SM<5%). The suspension was cooled to T=20-30° C., diluted with 100% ethanol (213.1 kg, 4.50–v/w SM), stirred 15 min at T=20-30° C., and finally centrifuged to remove the excess of carbonate and potassium bromide. The line and the cake were washed with 100% ethanol (82.4 kg, 1.74–v/w SM); then 50% hydroxylamine in water (48.8 kg, 1.5 equiv.) was added to the filtrate at room temperature, then the bulk was heated up to T=73-77° C. and stirred at this temperature for 2 hours. A sample was taken for IPC (Aca-11-aldehyde<5%), then the bulk was concentrated under reduced pressure (270-150 mbar, 45-55° C.) to ~6 Vol, the residue quenched with water (404.5 kg, 6.74–v/w SM) at T=45-55° C. and the residual ethanol distilled under vacuum (270-150 mbar, 45-55° C., residual Vol=~10.4). The bulk was diluted with benzene 60-90 (236.9 kg, 5.64–v/w SM) and heated at reflux (T=~60° C.) to reach a complete dissolution (~15 min, visual check). The solution was cooled down to 8-12° C. (crystallization occurs at T=~17° C., seed at ~12° C. if necessary), then to 0-5° C. After 2 hours stirring at T=0-5° C., the bulk was centrifuged and the cake washed with benzene 60-90 (59.4 kg, 1.41–v/w SM) in 2 portions, then dried under reduced pressure at T=40° C. to provide 86.7 kg (91.3%) of product.

c) Preparation of:

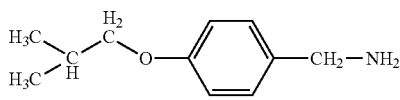

The product from step b (SM, 40.0 kg) was dissolved in 100% ethanol (229.5 kg, 7.26–v/w SM) at T=20-25° C., then anhydrous Raney-Nickel (5.8 kg, 14.6%–w/w SM) was added under nitrogen (wash the catalyst with 100% ethanol until KF<300 ppm) and the suspension cooled down to T=−8° C.-12° C. Ammonia gas (45.8 kg, 13 equiv.) was added under vacuum over ~8 hours through a cannula, then the suspension heated up to T=48-50° C. (the internal pressure rises to ~2.5 bar). The bulk was hydrogenated at T=48-50° C. and P=4 bar until the hydrogen absorption stops (~9 hours) and the residual SM was checked by HPLC (SM<0.5%). The suspension was cooled to T=10-15° C., the excess of ammonia was removed, the bulk was clarified (1575+GF92 filter papers+ celtroxe layer on the filter) and the line was washed with 100% ethanol (63.4 kg, 2.00–v/w SM). The solvent was distilled under reduced pressure (P=870-13 mbar, T=42-50° C.) and the oily green residue was diluted with 100% ethanol (50.7 kg, 1.60–v/w SM) and ethyl acetate (150.1 kg, 4.17–v/w SM) and finally cooled to T=20-25° C. 100% Acetic acid (19.9 kg, 1.60 equiv.) was slowly added allowing the temperature to rise during the addition (+~14° C.), then the bulk was heated to reflux (T=~70° C.) to reach a complete dissolution. The solution was cooled down to 40-42° C. and seeded, then the suspension was stirred at the crystallization temperature (T=~41° C.) for 30 min, cooled to T=0-5° C. and stirred 5 hours at this temperature. The bulk was centrifuged, the cake washed with cold ethyl acetate (2×9.4 kg, 2×0.26–v/w SM) and finally dried under vacuum at T=50° C. to provide 33.6 kg (67.9%) of amino acetate form.

A solution of the amino acetate form (26.4 kg) in potable water (42.2 kg, 1.60 Vol) was basified with 30% sodium hydroxide (35.4 kg, ~2.41 equiv.) to pH=14 at T=10-25° C., then the product was extracted in toluene (91.4 kg, 4.00 Vol) at T=43-47° C. The bulk was decanted at T=43-47° C., the pH was corrected to 14 with additional 30% NaOH if necessary, then phases were separated. The organic phase was washed with potable water (35.1 kg, 1.33 Vol), then concentrated to dryness under vacuum (P=170-20 mbar, indicative) at T=48-50° C. affording the product as an oily residue.

d) Preparation of:

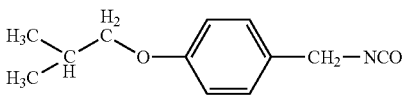

The product from step c was dissolved in anhydrous toluene (68.5 kg, KF<300 ppm, 3.00 Vol), the solution transferred into a phosgenation reactor equipped with scrubber and the line washed with anhydrous toluene (10.3 kg, 0.45 Vol). The toluene solution was cooled to T=0-5° C. and hydrogen chloride (gas, 4.0 kg, 1.00 equiv.) was slowly introduced in ~3 hours with a cannula at T max=10° C. At the end of the addition, the bulk was heated up to 97-103° C. and phosgene (16.6 kg, 1.5 equiv.) was slowly introduced (~3 hours) with a cannula. At the end of the addition, the mixture was stirred for additional 30 min at T=97-103° C., the reaction was checked by IPC (TLC, starting material<1%) and the bulk cooled down to T=80-85° C. The solution was concentrated under vacuum (P=500 mbar, indicative) at the same temperature to ~2.1 Vol, the bulk was checked to confirm the absence of residual phosgene and the crude isocyanate solution cooled to T=20-25° C., discharged into a drum and analyzed.

e) Preparation of the Title Compound of Formula IV:

The product from step d (~30% toluene solution, 1 equiv.) was added in ~40 min at T=38-42° C. to a solution of the product from step a (SM, 21.8 kg) in THF (189.5 kg, 9.80–v/w SM). At the end of the addition, the line was washed with THF (9.7 kg, 0.50–v/w SM), the bulk was stirred at T=38-42° C. until a clear solution was obtained (~3 hours) and a sample was taken for IPC (TLC, Aca-11-Fluoramine<1%) to check completeness of the urea formation. The solvent was distilled under reduced pressure (P=170-70 mbar, T=22-25° C.) and the solid residue was dissolved in 100% ethanol (132.5 kg, 7.69–v/w SM) at T=40-45° C. A previously prepared solution of L-(+)-tartaric acid (8.1 kg, 1.10 equiv.) in 100% ethanol (96.0 kg, 5.57–v/w SM) was added at T=40-45° C. and the line was washed with 100% ethanol (3.3 kg, 0.19–v/w SM). The solution was cooled down to 35-38° C. and seeded, the suspension was stirred at the crystallization temperature (T=~37° C.) for 30 min, cooled to T=0-5° C. in ~2 hours and finally stirred at this temperature for additional 2 hours. The bulk was centrifuged, the cake washed with cold 100% ethanol (2×18.9 kg, 2×0.65–v/w SM) and the dry weight of the crude product was calculated based on LOD (~46%).

Crude tartrate product (36.7 kg, SM, dry weight calculated based on measured LOD) was dissolved at reflux (T=~75° C.) in 100% ethanol (205.4 kg, 7.08–v/w SM, alcohol contained in wet product included), then the solution was filtered at reflux temperature through an absolute 0.3μ cartridge and the line rinsed with hot 100% ethanol (5.9 kg, 0.21–v/w SM). The solution was cooled down to 48-50° C. and seeded, the suspension was stirred at the crystallization temperature (T=~49° C.) for 30 min, cooled in ~2 hours to T=20-22° C. and finally stirred at this temperature for additional 2 hours. The bulk was centrifuged, the cake washed with pre-filtered cold 100% ethanol (2×18.9 kg, 2×0.65–v/w SM) and the product dried under vacuum at T=45° C. for at least 60 hours.

A suspension of the compound of formula IV (SM, 26.5 kg) in pre-filtered and degassed methyl ethyl ketone (149.3 kg, 7.00 Vol) was heated to T=58-63° C. and stirred at this temperature for 8 hours under nitrogen atmosphere. Samples for IPC (powder X-ray, DSC, IR) were taken each 2 hours stirring. The mixture was cooled down to T=12-17° C. in ~4.5 hours and stirred at this temperature for ~2 hours, then the product was centrifuged and the cake washed with cold (15° C.) pre-filtered and degassed methyl ethyl ketone (2×10.7 kg, 2×0.50 Vol). The wet product was dried ~15 hours in vacuo at T=45° C., discharged and packaged under nitrogen to provide 25.2 kg (51.1%) of Form C of the title compound of formula IV.

What is claimed is:

1. Crystalline form C of N-(4-fluorobenzyl)-N-(1-methylpiperidin-4-yl)-N'-(4-(2-methylpropyloxy)phenylmethyl) carbamide tartrate of formula IV,

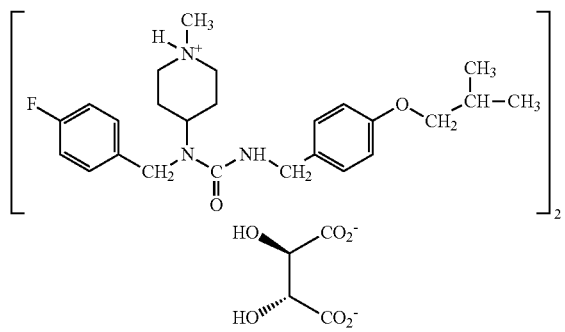

(IV)

which shows an endothermic signal at 177° C. as measured by differential scanning calorimetry.

2. The crystalline form of claim 1, wherein the endothermic signal at 177° C. has an enthalpy of fusion of about 129 J/g.

3. The crystalline form of claim 1, wherein the endothermic signal at 177° C. is a melting temperature.

4. The crystalline form of claim 1, which results in a weight loss of about 0.9% below 150° C. as measured by thermogravimetric analysis.

5. The crystalline form of claim 1 that has less than 1000 ppm of residual solvent.

6. The crystalline form of claim 1 that has less than 200 ppm of residual solvent.

* * * * *